United States Patent [19]
Pon

[11] Patent Number: 5,428,699
[45] Date of Patent: Jun. 27, 1995

[54] PROBE HAVING OPTICAL FIBER FOR LATERALLY DIRECTING LASER BEAM

[75] Inventor: Russell Pon, Santa Clara, Calif.

[73] Assignee: Laserscope, San Jose, Calif.

[21] Appl. No.: 86,014

[22] Filed: Jul. 2, 1993

[51] Int. Cl.⁶ .............................................. G02B 6/26
[52] U.S. Cl. ..................................... 385/31; 385/901; 385/47; 385/39; 128/6; 606/7
[58] Field of Search ....................... 385/31, 36, 38, 39, 385/47, 901; 128/6; 606/17, 15, 16, 7

[56] References Cited

U.S. PATENT DOCUMENTS

| | | | |
|---|---|---|---|
| 4,273,127 | 6/1981 | Auth et al. | 128/303.1 |
| 4,566,438 | 1/1986 | Liese et al. | 128/6 |
| 4,620,547 | 11/1986 | Boebel | 128/754 |
| 4,669,467 | 6/1987 | Willett et al. | 128/303.1 |
| 4,740,047 | 4/1988 | Abe et al. | 350/96.15 |
| 4,819,632 | 4/1989 | Davies | 128/303.1 |
| 4,832,979 | 5/1989 | Hoshino | 427/38 |
| 4,852,567 | 8/1989 | Sinofksy | 128/303.1 |
| 5,000,752 | 3/1991 | Hoskin et al. | 606/9 |
| 5,041,121 | 8/1991 | Wondrazek et al. | 606/128 |
| 5,093,877 | 3/1992 | Aita et al. | 385/34 |
| 5,253,312 | 10/1993 | Payne et al. | 385/901 X |

FOREIGN PATENT DOCUMENTS

| | | |
|---|---|---|
| 0163266A2 | 5/1985 | European Pat. Off. . |
| 61-219904 | 9/1986 | Japan ............................. G02B 6/10 |
| 3-63377 | 9/1991 | Japan . |

Primary Examiner—Frank Gonzalez
Assistant Examiner—Phan Thi Heartney Palmer
Attorney, Agent, or Firm—Haynes & Davis

[57] ABSTRACT

An improved optical fiber for laterally directing a laser beam having a waveguide including a tip for communicating electromagnetic radiation in a propagation direction to the tip of the waveguide, a transmitting surface on the tip of the waveguide, a reflecting surface on the tip of the waveguide for internally reflecting electromagnetic radiation communicated by the waveguide in a direction lateral to the propagation direction toward a particular area on the transmitting surface, and wherein the particular area and the reflecting surface are disposed so that substantially all electromagnetic radiation reflected by the reflecting surface is incident on the particular area at below a critical angle for transmission through the transmitting surface in the lateral direction. By preventing electromagnetic radiation from being incident on the transmitting surface above a critical angle, the present invention prevents internal reflection off the transmitting surface and improves the efficiency of the laterally directing probe.

34 Claims, 11 Drawing Sheets

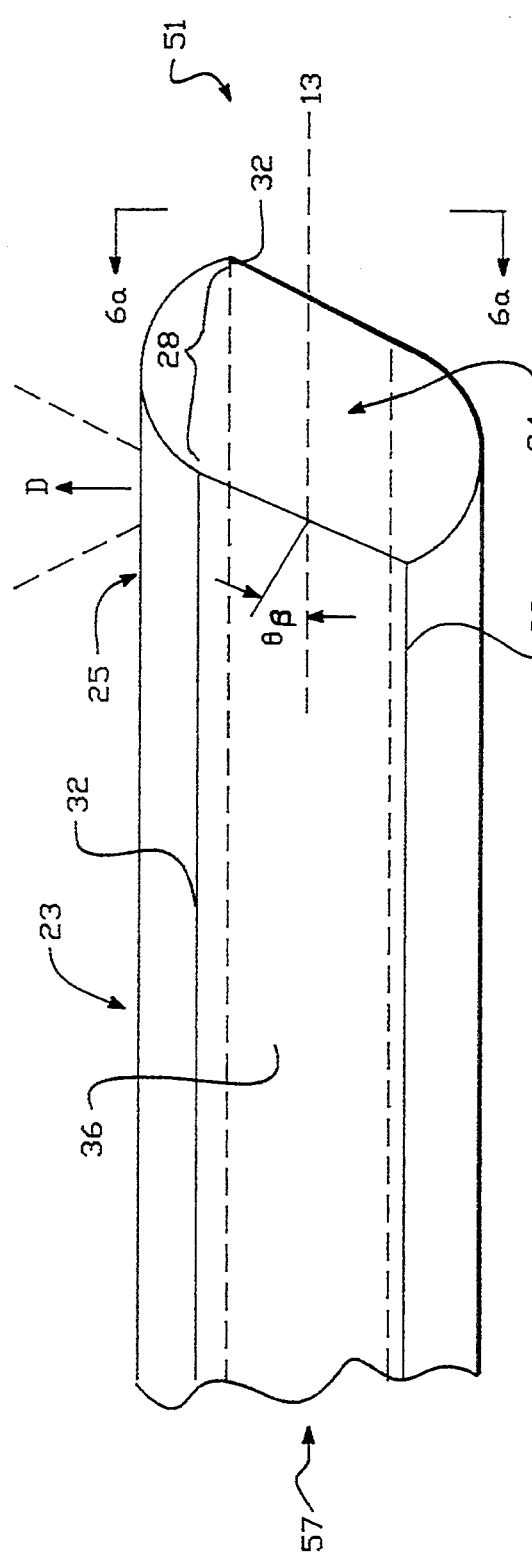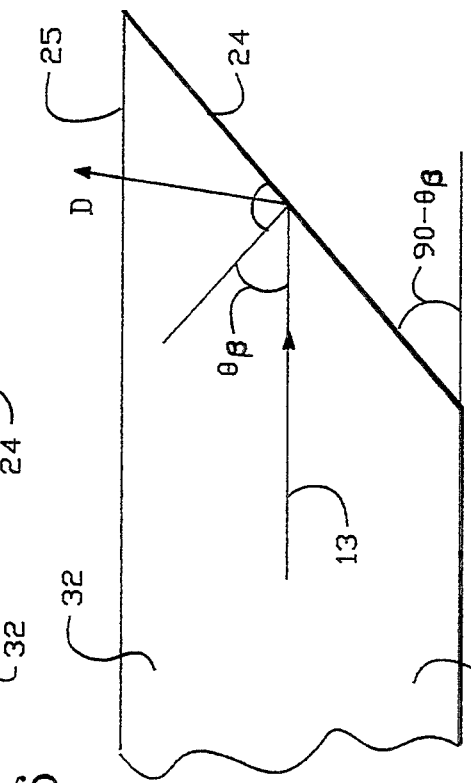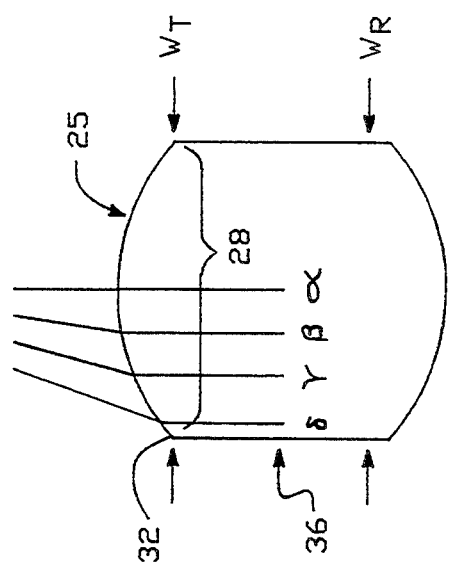
FIG.6
FIG.6b
FIG.6a

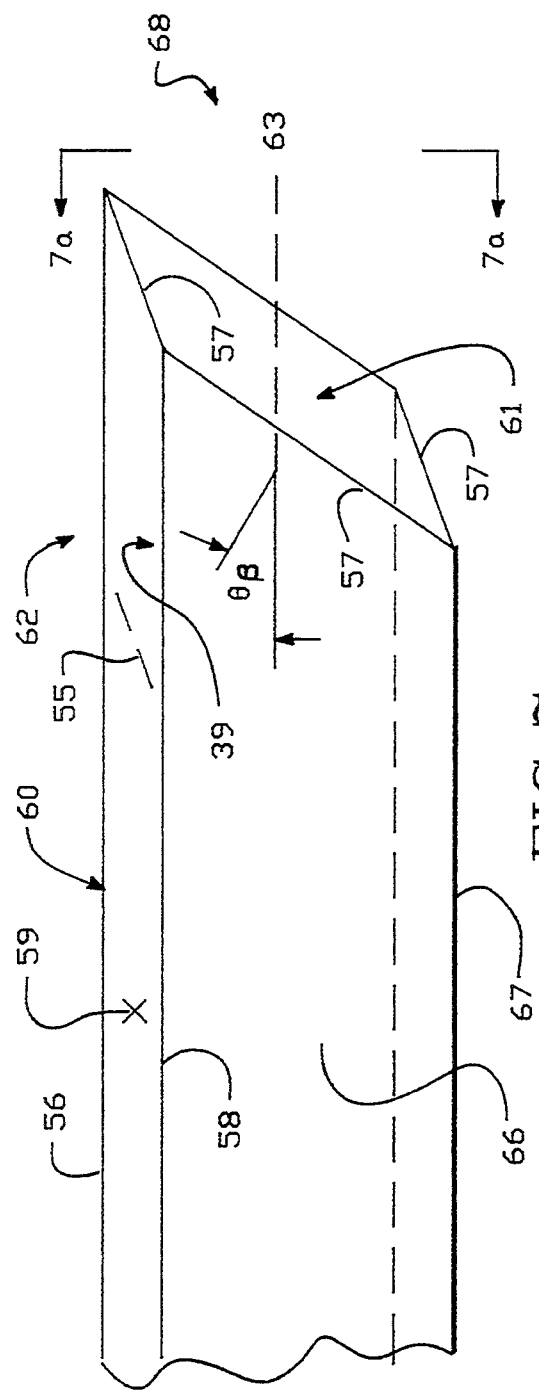
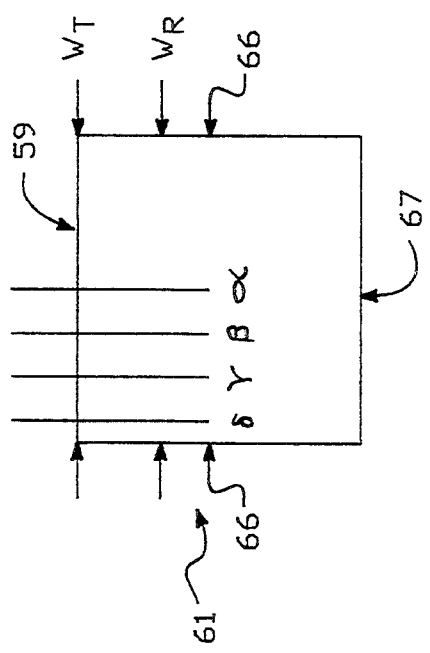
FIG. 7
FIG. 7a

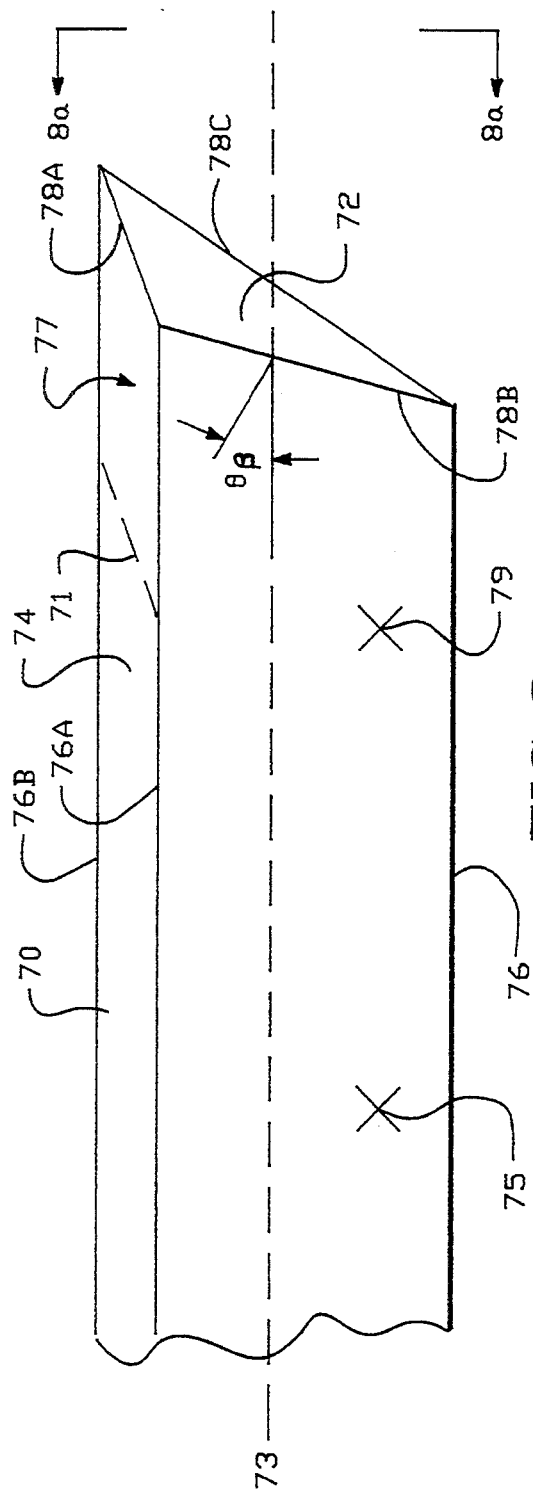
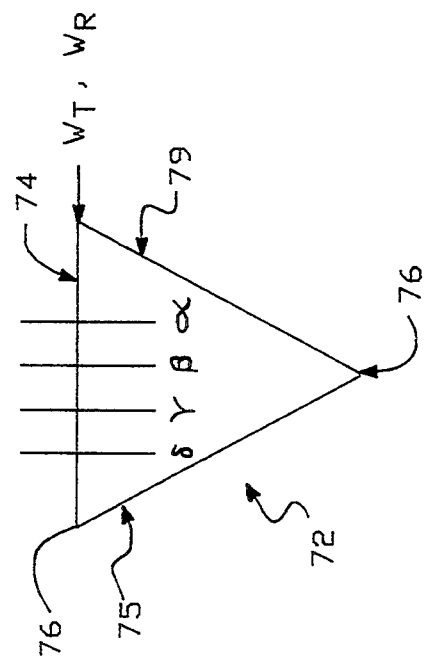
FIG. 8
FIG. 8a

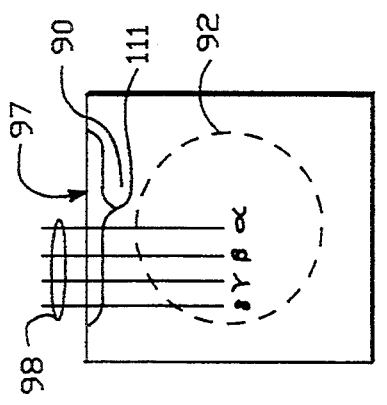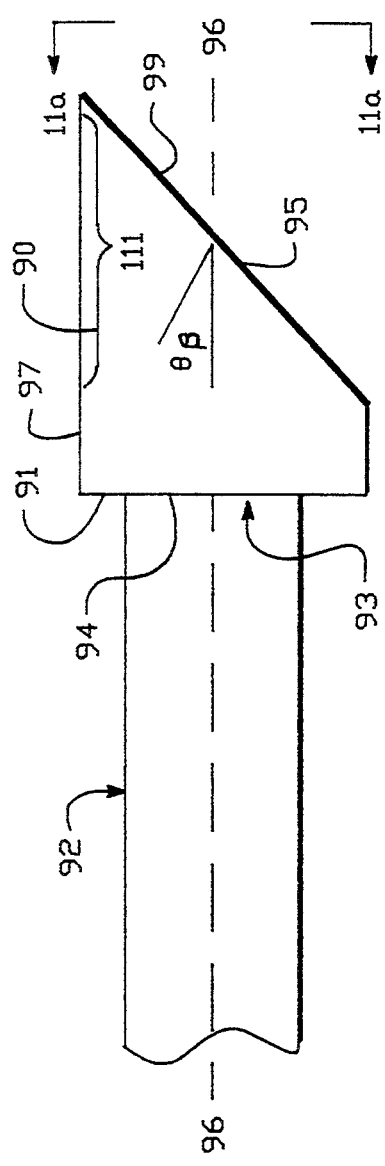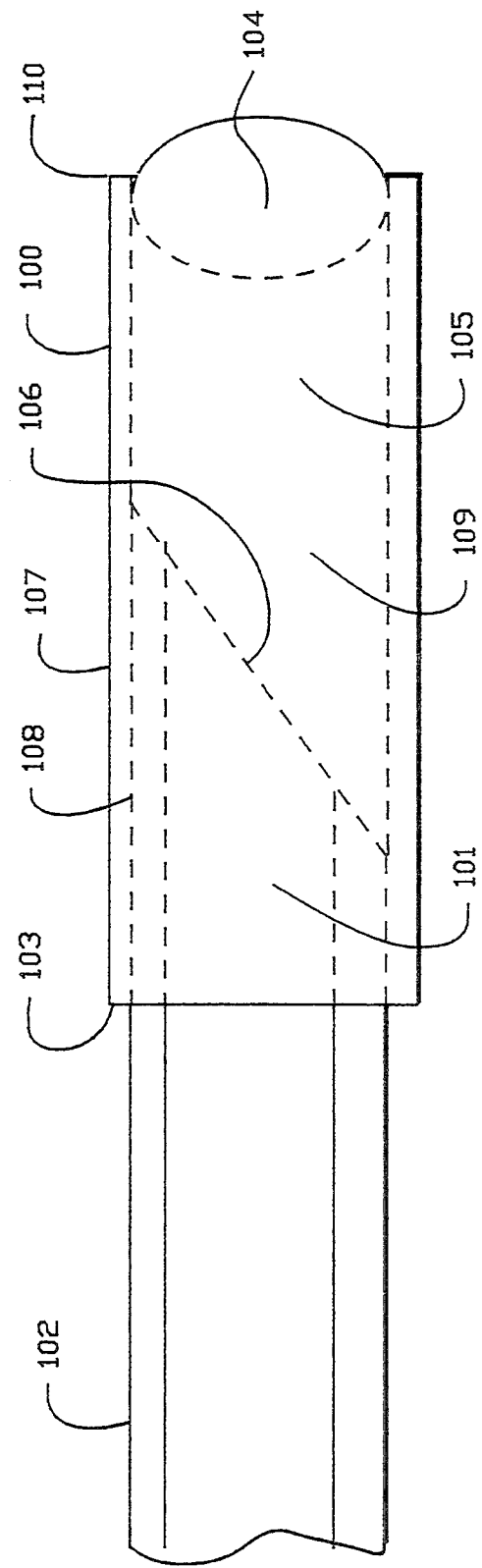

PROBE HAVING OPTICAL FIBER FOR LATERALLY DIRECTING LASER BEAM

FIELD OF THE INVENTION

The present invention relates generally to surgical probes that laterally direct laser energy, and more particularly, to optical fibers within such probes that include a tip for laterally directing laser energy being transmitted through the optical fiber.

DESCRIPTION OF RELATED ART

In typical medical procedures using laser energy, a surgical probe is positioned at a location near the portion of body tissue to be treated with laser energy. After the surgical probe has been appropriately positioned, an optical fiber or waveguide for communicating laser energy is inserted through a cannula in the probe to the position within the patient that is to be treated. In many of these medical procedures, it is necessary for the laser energy to be directed laterally from the tip of the probe.

One of the medical procedures that uses a probe having a laterally directing tip is for the treatment of Benign Prostatic Hyperplasia (BPH) which causes an abnormally enlarged prostate gland. An enlarged prostate gland can cause difficulty in urination and even retrograde ejaculation. Since approximately 50 percent of all men over 50 years of age will suffer from an enlarged prostate gland, development of more effective and less traumatic treatment procedures is very important.

One progressive technique for treating BPH utilizes a laser probe having an optical fiber coupled to a laser source that is inserted into the urethra so that the tip is positioned adjacent to the prostate gland. Laser energy is then laterally directed out of the tip of the optical fiber onto desired portions of the enlarged prostate gland in order to cause necrosis of the tissue. The destroyed tissue sloughs off into tiny particles that pass out through the urethra of the patient during urination.

One prior art design for laterally directing laser energy from the distal end of an optical fiber is disclosed in U.S. Pat. No. 4,740,047, issued to Abe, et al. The distal end of the cylindrical optical fiber is bevelled in order to laterally reflect laser energy being communicated by the fiber. However, a significant portion of the laser energy or beam does not leave the fiber in the desired direction due to internal reflection of the beam off interfaces between the fiber and the surrounding environment.

The Abe, et al. patent attempts to prevent misdirected laser energy from damaging patient tissue by using a protective, transparent cap that encloses the distal end of the optical fiber and includes specially arranged reflective and anti-reflective coatings. The reflective and anti-reflective coating layers, taught by the Abe, et al. patent, however, can melt at high temperatures or carbonize during tissue irradiating procedures. If the coating layers become carbonized, then the amount of energy that can be delivered to the desired tissue location is reduced and an increased amount of energy is absorbed, resulting in further heating of the probe. The resulting heating of the probe limits the amount of energy that can be used in order to prevent burning the patient, the probe, or both.

In view of the above-discussed problems associated with prior art laterally directing fiber tips, an improved fiber tip for laterally directing a laser beam is desired.

SUMMARY OF THE INVENTION

The present invention provides an improved optical fiber tip for laterally directing a laser beam. The present invention comprises a waveguide, such as an optical fiber, having a tip. Electromagnetic radiation propagates in a propagation direction along the waveguide to the tip. The tip includes a transmitting surface and a reflecting surface. The reflecting surface is disposed so that electromagnetic radiation is internally reflected in a lateral direction relative to the propagation direction toward a particular area on the transmitting surface. The electromagnetic radiation propagating in the lateral direction is incident on the particular area of the transmitting surface at below the critical angle. Thus, the reflecting surface and the transmitting surface are disposed so that substantially all electromagnetic radiation reflected by the reflecting surface is incident on the particular area at below a critical angle for transmission through the transmitting surface in the lateral direction. In one aspect of the invention, greater than 90% of the measured output energy is directed in the desired lateral direction, greatly improving over prior art systems.

According to one embodiment of the invention, the waveguide includes an optical fiber having a bevelled distal end. The distal end of the tip is bevelled at an angle relative to the propagation direction of the radiation so that substantially all the radiation is internally reflected onto a particular area of the transmitting surface. In one configuration, the tip includes two opposing flat sides in respective planes parallel to the propagation direction and the opposing flat sides extend to the reflecting surface. The particular area of the transmitting surface comprises an arced surface extending to and intersecting the opposing flat sides and the bevelled end so the particular area is limited by the intersection of the two opposing flat sides and the bevelled end.

According to another configuration, the waveguide comprises a fiber optic including a fiber core within which radiation transmitted through the fiber is confined, and a cladding layer over the fiber core. The cladding layer has a predetermined thickness relative to the radius of the fiber core. The fiber optic is bevelled such that the reflecting surface is defined by the end of the fiber core. Substantially all of the reflected radiation is transmitted through the interface between the fiber core and cladding layer. The transmitting surface lies on the outside surface of the cladding layer. The radius of the outside surface of the cladding layer is large enough relative to the radius of the fiber core such that electromagnetic radiation reflected by the reflecting surface is incident on the particular area on the transmitting surface of the cladding at below a critical angle.

According to another aspect of the invention, the tip is a separate component that is coupled to the distal end of the waveguide.

According to a further aspect of the invention, the transmitting surface and the reflecting surface are enclosed by a transparent cap forming a cavity adjacent to the reflecting surface, and the cavity contains a predetermined medium adjacent to the reflecting surface so as to maintain a predetermined index of refraction for the reflecting surface.

Other aspects and advantages of the present invention can be seen upon review of the figures, the detailed description, and the claims which follow.

BRIEF DESCRIPTION OF THE FIGURES

FIG. 6 is a perspective view of an optical fiber tip configured in accordance with a first embodiment of the present invention.

FIG. 6a is an end view of the optical fiber tip taken along line 6a–6a of FIG. 6.

FIG. 6b is a side view of the fiber tip of FIG. 6.

FIG. 7 is a perspective view of an optical fiber tip configured in accordance with a second embodiment of the present invention.

FIG. 7a is an end view of the optical fiber tip taken along line 7a–7a of FIG. 7.

FIG. 8 is a perspective view of an optical fiber tip configured in accordance with a third embodiment of the present invention.

FIG. 8a is an end view of the optical fiber tip taken along line 8a–8a of FIG. 8.

FIG. 11 is a side view an embodiment for coupling a tip to the distal end of the waveguide in accordance with the present invention.

FIG. 11a is an end view of the tip taken along line 11a–11a of FIG. 11.

FIG. 12 is a side view of a further embodiment of the present invention wherein a tube is coupled to the tip of the waveguide.

DESCRIPTION OF THE PREFERRED EMBODIMENTS

Figure 1:
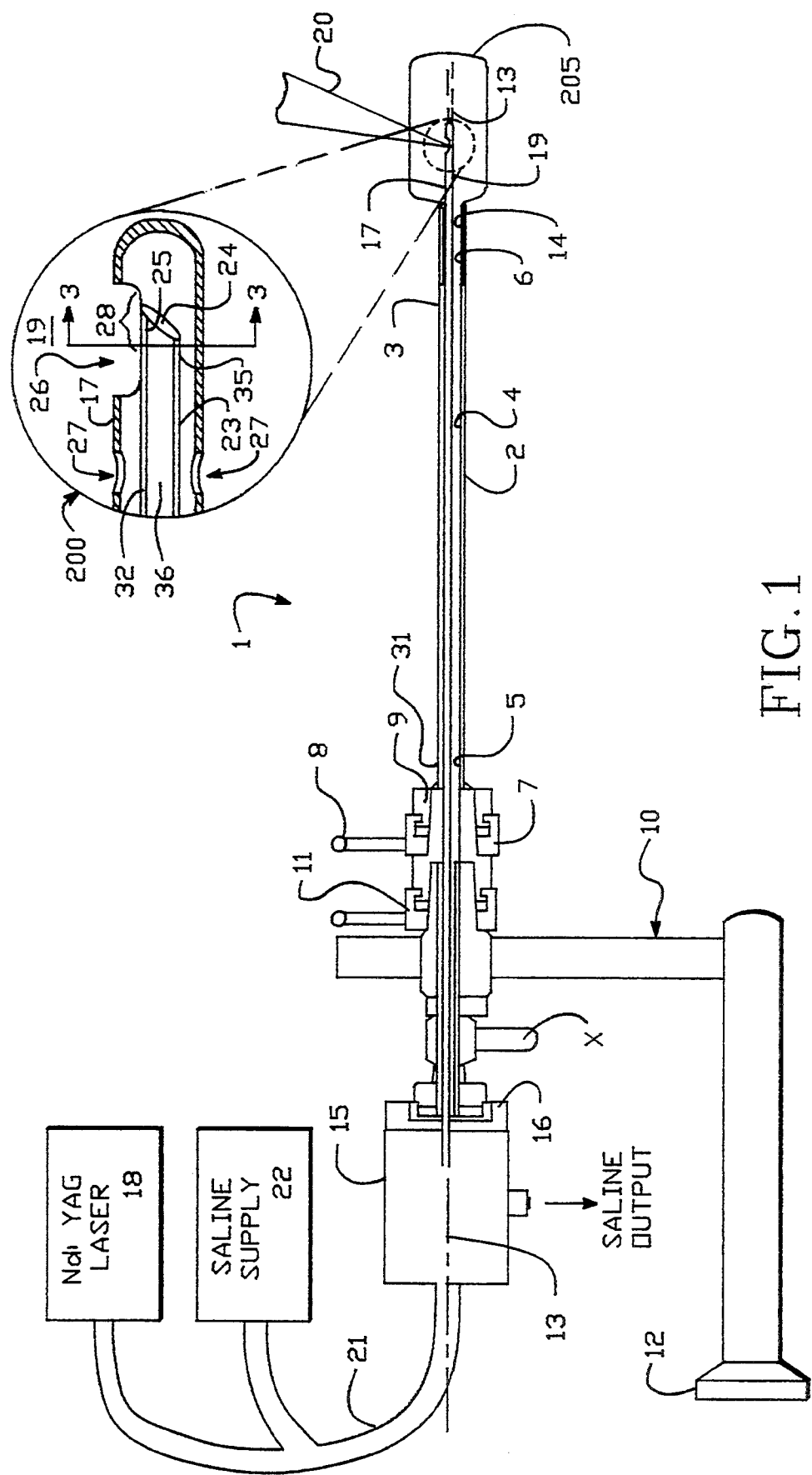
FIG. 1 is a surgical probe incorporating the present invention and including an enlarged view of one embodiment of the distal end with a laterally directing tip.

Turning now to the drawings, FIG. 1 shows a surgical tool 1 incorporating the present invention. The surgical tool 1 includes an outer sheath 2 having a distal end 3 and a proximal end 31. The surgical tool 1 can be used, for example, in treatment of the prostate gland, wherein the distal end 3 is inserted into the urethra of the patient and positioned at a region adjacent to the prostate gland. Preferably, outer sheath 2 is formed of series 300 stainless steel, but may be made with aluminum, thermal plastics, or other materials. The outer sheath has a circular cross-section with a diameter sufficient to support the components of surgical tool 1.

A cannula 4 is positioned within sheath 2. Cannula 4 has a circular cross-section, a proximal end 5 and a distal end 6 coincident with the proximal end 31 and distal end 3 of outer sheath 2, respectively. Bayonet mount 7, coupled to proximal end 31 of sheath 2, secures cannula 4 in sheath 2. Positioning grip 8 is attached to bayonet mount 7. Grip 8 is utilized to allow mount 7, and cannula 4, to be secured to outer sheath 2. Mount 7 couples about a notched ring 9 attached to proximal end 31 of sheath 2.

A scope assembly 10 may be included and secured to bayonet mount 7 by a second bayonet mount 11. Scope assembly 10 includes an eyepiece 12 which is offset in this embodiment from longitudinal axis 13, wherein longitudinal axis 13 is defined by the length of sheath 2 at the center point circular cross-section thereof. Scope assembly 10 includes viewing channel 14 which is positioned in cannula 4 and extends from the eyepiece 12 of scope assembly 10 to the distal end of sheath 2. Scope assembly 10 may be of the type manufactured by Karl Storz Endoscopy-America, Inc., Culver City, Calif. Other scopes may be used, such as an Albarran bridge or other cystoscopes. An in-line scope may be preferred in some applications.

A probe 17 is also provided in cannula 4, and the probe 17 includes a fiber optic for communicating or transmitting laser energy to the distal end 19 of the probe, and laterally directing the laser energy 20 onto the surgical site. The probe 17 can be a rigid cannula or a flexible catheter. The fiber optic and a saline supply tube are coupled to probe handle 15 and are encased in a flexible plastic tube 21. The fiber optic is coupled to a laser energy source 18. The tube 21 couples a source of pressurized saline 22 to probe 17. The pressurized saline 22 is used to inflate balloon 205 which is coupled to the distal end 6 of cannula 4. When inflated, the balloon 205 functions to secure the cannula 4 position within the urethra and other purposed known in the art.

In a surgical procedure involving instrument 1, such as for an enlarged prostate gland, sheath 2 is first placed into the urethra with an obturator positioned therein. The obturator (not shown) provides a sealed, rounded end piece at distal end 3 of sheath 2 to allow sheath 2 to be inserted into the urethra, by ensuring that distal end 3 of sheath 2 does not encounter resistance as it passes up the urethra, and reducing the risk of injury. Direct visualization or ultrasound imaging may be used to position distal end 3 of sheath 2 at a region adjacent the prostate gland. Once the sheath 2 is positioned in the urethra, the obturator is removed and the cannula 4, probe 17, and viewing channel 14 are inserted into the sheath 2 and secured by mount 7. The fiber optic, laser source 18, and saline supply 22 are attached to the handle 15, and the handle 15 is attached to the scope assembly 1 0, prior to attaching the scope assembly 10 to the sheath 2. Laser energy may be provided by an Nd:YAG laser having an output power of about 40–100 watts.

According to the present invention, improved means for laterally directing the laser energy 20 are included at the distal end 19 of the probe 17. An enlarged view, generally 200, of the distal end 19 of the probe 17 is shown in FIG. 1. An optical fiber 23 is positioned within the probe 17 through which electromagnetic radiation is transmitted to the distal end 19 of the probe 17 from the laser source 18.

Any plastic cladding near the distal end of the fiber optic is removed, and the distal end of the optical fiber 23 is bevelled to form a reflecting surface 24 for internally reflecting electromagnetic radiation such as a laser beam or other intense light energy. The reflecting surface 24 internally reflects light energy being communicated by the fiber 23 so as to be incident on a transmitting surface 25 disposed in the peripheral surface of the fiber core 23. A particular area 28 of the internal side of the transmitting surface 25 receives light rays reflected by the reflecting surface 24. The particular area 28 is disposed relative to the reflecting surface 24 so that substantially all electromagnetic radiation reflected by the reflecting surface 24 is incident on the particular area 28 at below a critical angle for transmission through the transmitting surface 25 and through the cut out 26 of the probe 17.

The tip of the waveguide is configured such that substantially all electromagnetic radiation or light rays internally reflected by the reflecting surface 24 are incident on the transmitting surface 25 of the tip at an angle of incidence less than the critical angle, thereby preventing internal reflection off the transmitting surface 25. A more detailed discussion of the "critical angle" is provided below in reference to FIGS. 5a-5c and 10. As may be realized, there are various configurations for waveguides that satisfy the required specifications.

The fiber 23 shown in FIG. 1 illustrates one embodiment configured in accordance with the invention. The exterior surface perimeter of the fiber core 23 includes two flat sides 36 that are parallel to the direction of light energy reflected by the reflecting surface 25. The flat sides 36 intersect arced surfaces 35 (see also FIG. 3) of the fiber 23 at longitudinal edges 32. The particular area 28 is limited by the intersection of the transmitting surface 25 with the flat sides 36 and the bevelled end or reflecting surface 24.

The flat sides of the fiber 23 limit the width of the reflecting surface, preventing light energy from being incident on the particular area 28 at above a critical angle. As a result, all light energy reflected by the reflecting surface 25 is incident on the particular area 28 of the transmitting surface 25 below the critical angle and thus passes through the transmitting surface 25. A more detailed discussion of the distal end of the fiber 23 is provided below in reference to FIGS. 6 and 6a.

Openings 27 are included in the probe 17 for aspiration and irrigation purposes. The openings 27 are circular in the illustrated embodiment and enable air or liquid to pass between the ambient environment and the interior 37 of the probe 17.

Figure 2:
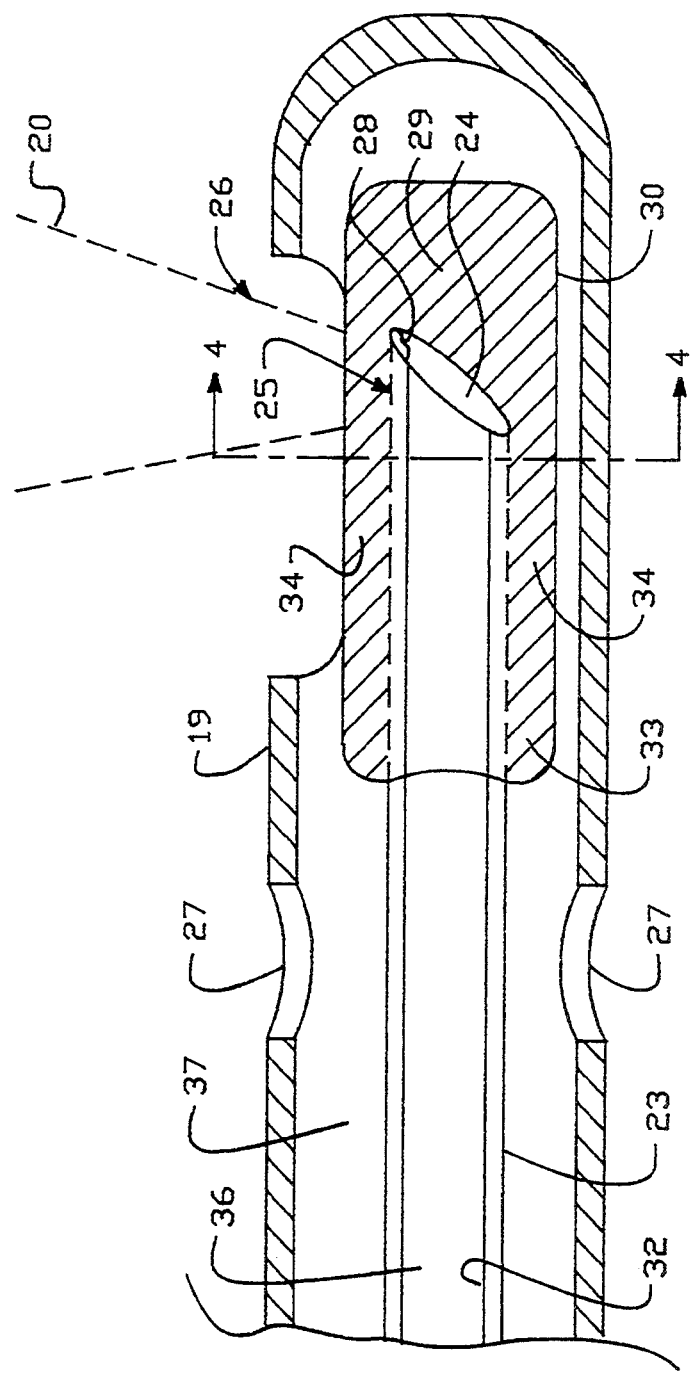
FIG. 2 is an alternative embodiment of the enlarged distal end shown in FIG. 1.

FIG. 2 illustrates an alternative embodiment wherein a cap 30 is secured around the distal end or tip of the fiber 23. The cap 30 is constructed of a transparent material, such as quartz or glass. Prior, co-pending U.S. patent application Ser. No. 07/614,358 invented by Fletcher, et al., filed Nov. 15, 1992, and owned by the same Assignee as the present application, describes one such cap and is incorporated by reference.

The transparent cap 30 encloses the transmitting surface 25 and the bevelled end or surface 24 of the fiber 23. A cavity 29 is formed within the cap 30 in order to maintain a selected medium, such as air, adjacent to the bevelled end 24. By maintaining a selected medium, a predetermined ratio of indices of refraction also can be maintained between the reflecting surface 24 and the cavity 29.

Figure 3:
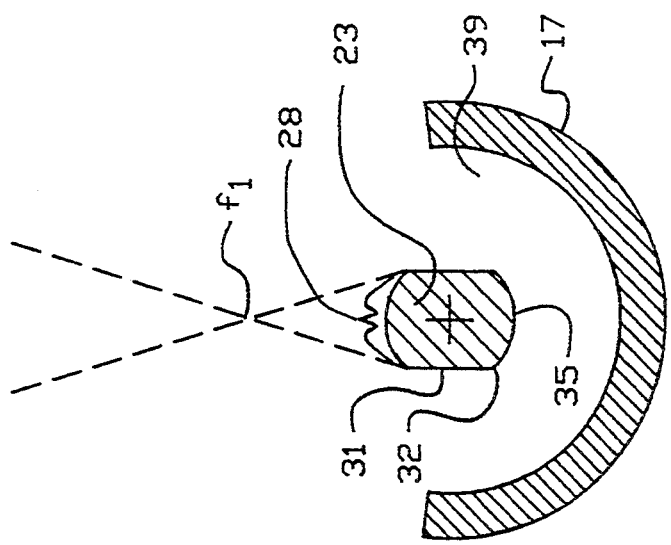
FIG. 3 is a cross-sectional view of the distal end taken along line 3—3 of FIG. 1.

A proximal end 33 of the cap 30 is secured to the fiber 23 by an optically transparent adhesive 34. If the adhesive 34 covers the transmitting surface 25, as illustrated in FIG. 3, then the adhesive 34 is preferably index matched to the fiber material and the cap material so as to avoid refracting or reflecting electromagnetic radiation at the interface between the fiber 23 and the transparent adhesive 34, or the interface between the transparent adhesive 34 and the cap 30. Electromagnetic radiation, internally reflected by the reflecting surface 25, passes through the particular area 28 of the transmitting surface 25, the adhesive 34, the cap 30, and then through the cut out 26 as shown by light energy path 20.

Figure 4:
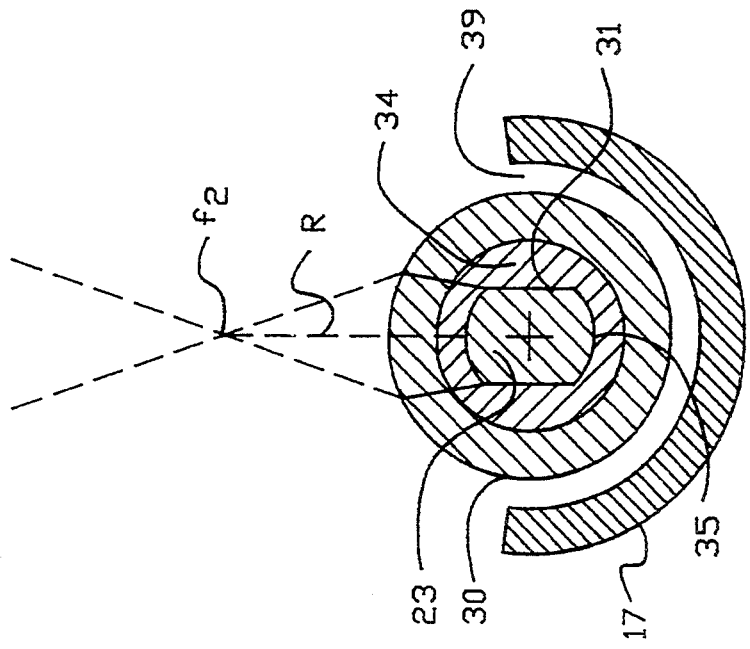
FIG. 4 is a cross-sectional view of the distal end taken along line 4—4 of FIG. 2.

FIGS. 3 and 4 are cross-sections of the embodiments shown in FIGS. 1 and 2, respectively. FIG. 4 shows the focal point f2 of laser energy wherein the cap 30 is included, and FIG. 3 illustrates the focal point f1 wherein a cap is not included. Both FIGS. 3 and 4 illustrate spacing 39 between the fiber 23 (or cap) and the probe 17. The cross-section of the probe 17 shown in FIGS. 3 and 4 is not a complete circle because the illustrated cross-sectional planes are positioned within the cut out 26 of the probe 17. Also illustrated in FIGS. 3 and 4 are the flat sides 36 and the arced surfaces 35 positioned between the flat sides 36. Longitudinal edges 32 are formed at the junction between the arced surfaces 35 and the flat sides 36. The upper illustrated arced surface 35 includes the particular area 28 of the transmitting surface 25.

As shown by focal point f2 in the cross-sectional plane shown in FIG. 4, electromagnetic radiation or light is focused further away from the optical fiber 23 using the transparent cap 30 because the focal point distance is proportional to the larger radius of the transparent cap 30 in FIG. 4 as compared with the radius of the fiber 23 in FIG. 3. Accordingly, the cap 30 changes the focal point in addition to enclosing the transmitting surface 25 and the reflecting surface 24. A predetermined focal point f2 of radius R is thereby achieved by using a cap 30 having the necessary thickness.

Figure 5B:
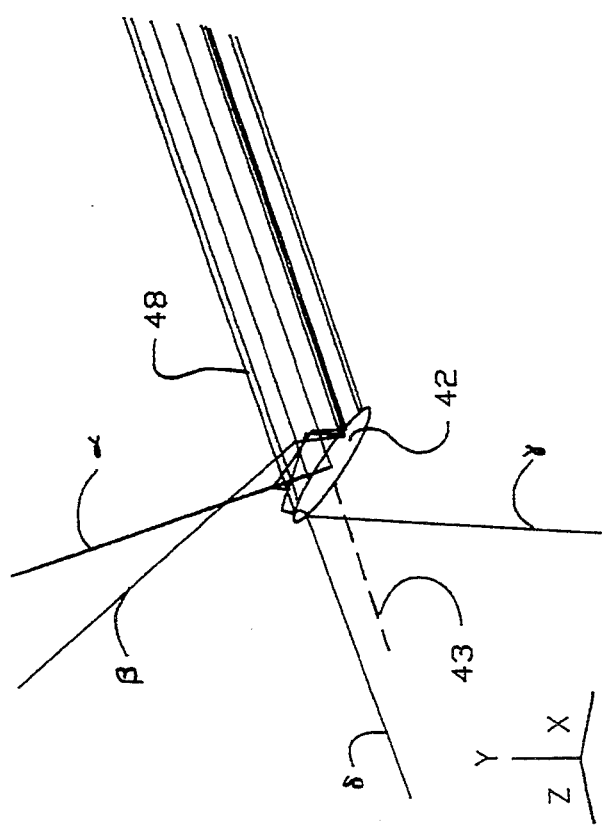
FIGS. 5a–5c provide light ray reflection diagrams for a prior art cylindrical optical fiber having a bevelled end.
Figure 5A:
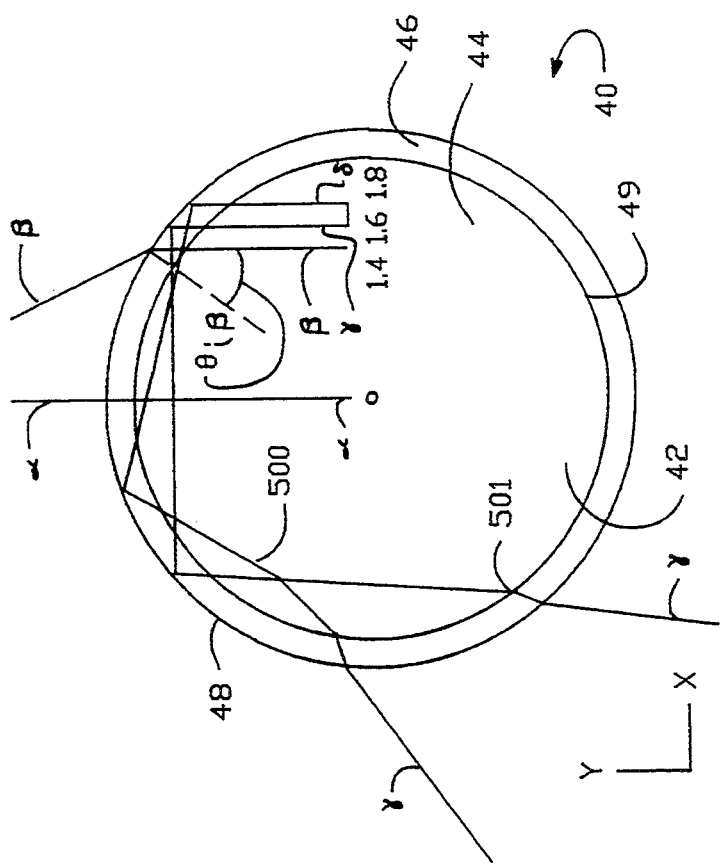
Figure 5C:
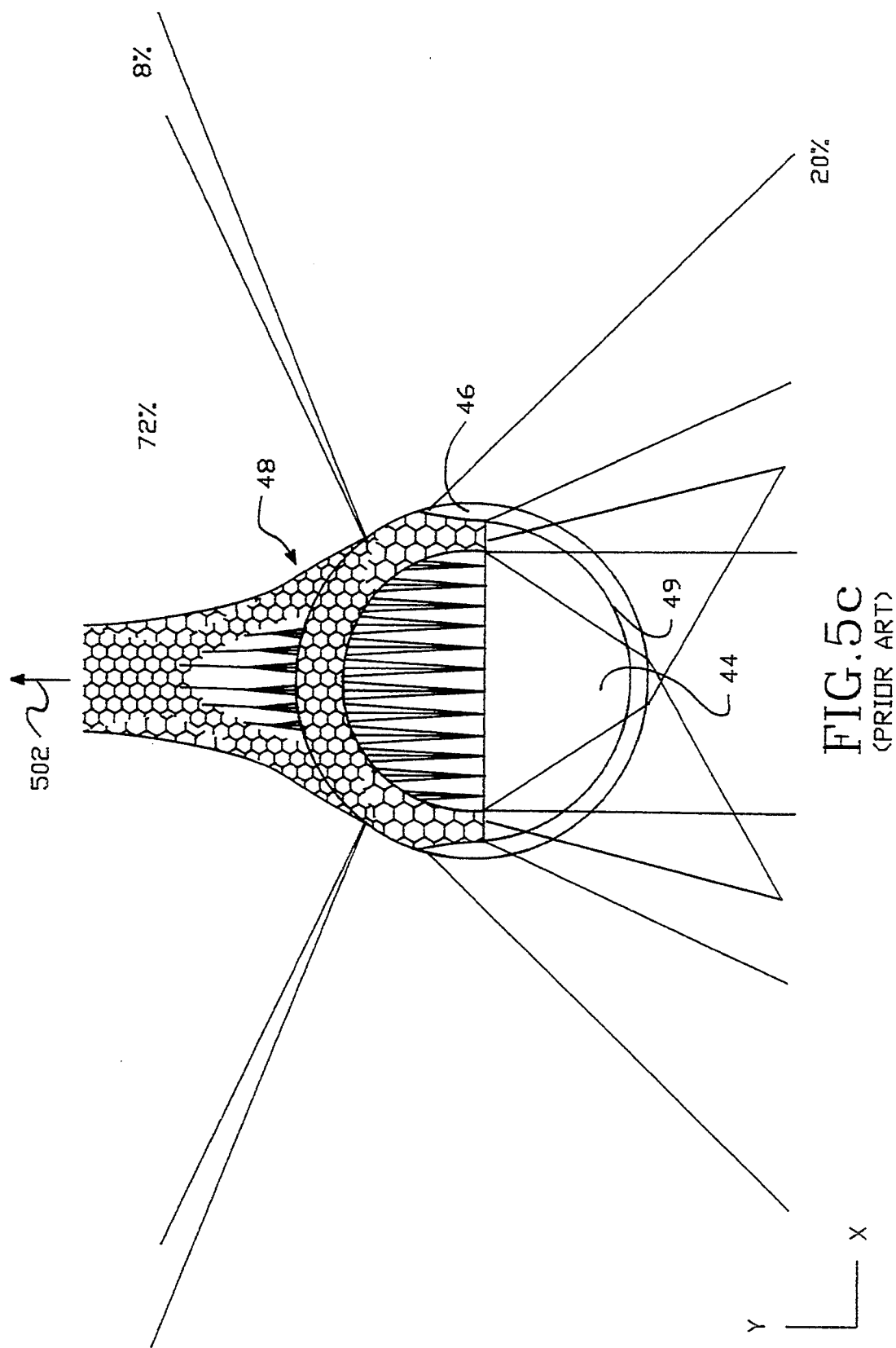

Referring now to FIGS. 5a-5c, these drawings illustrate different views of a cylindrical optical fiber 40 with a fused silica fiber core 44 and a doped fused silica cladding layer 46. The fiber has a bevelled end 42 defining a reflecting surface. FIGS. 5a-5c also illustrate the paths of electromagnetic radiation communicated by the prior art fiber 40. FIG. 5a is an end view of the bevelled end 42 looking along the Z-axis of the illustrated coordinate system, wherein an optical fiber core 44 is enclosed in a cladding 46. The cladding layer 46 has a slightly different index of refraction than the fiber core 44 establishing a refraction interface 49 between the two, and confining radiation transmitted through the fiber to the fiber core 44.

FIG. 5b more clearly illustrates the bevelled end 42 for internally reflecting and laterally directing a laser beam communicated by the optical fiber 40. A longitudinal axis 43 of the tip is illustrated in FIG. 5b for reference. Light rays or beams are communicated through the core 44 of the fiber 40 until they are internally reflected off the bevelled end 42 and directed in a lateral direction out the transmitting surface 48 of cladding 46. Light beams are reflected off the bevelled end 42 due to the different indices of refraction existing between the fiber 40 and the external environment (such as air) and the angle of the bevel relative to the propagation direction of the light beams.

When a light ray is incident on an interface between substances having different indices of refraction, the light beam is reflected or refracted. The angle of refraction $\theta_r$ is defined by Snell's law, wherein $N_i \sin \theta_i = N_r \sin \theta_r$. In Snell's law, $N_i$ is the index of refraction for the first or incident medium, $N_r$ is the index of refraction for the second medium, $\theta_i$ is the angle of incidence, and $\theta_r$ is the angle of refraction. When the angle of refraction ($\theta_r$) reaches 90°, the angle of incidence ($\theta_i$) is equal to the "critical angle." For angles of incidence in excess of the critical angle, essentially all of the light is internally reflected. The critical angle is the smallest angle from a line normal to the reflecting surface at which total reflection occurs. According to Snell's law, the critical angle ($\theta_c$) is equal to arcsin $N_r/N_i$.

In order for the bevelled end 42 to reflect all light energy being communicated by the fiber 40, the bevelled end 42 must be at an angle above the critical angle as determined by a relation of the indices of refraction between the optical fiber material and the surrounding medium, so that the light is internally reflected off the bevelled end 42 at an angle lateral to the longitudinal axis 43.

While it is desirable for all of the light rays being communicated by the optical fiber 40 to be completely internally reflected off the bevelled end 42 and laterally directed out the surface 48, such a result does not occur using a fiber optic as taught according to the prior art. The reason for this is that due to the cylindrical configuration of conventional optical fibers, the angle at which a substantial amount of reflected waves are incident on the transmitting surface 48 can result in a second undesired internal reflection causing a significant portion of the light energy to be directed in undesired directions. These reflected waves can also be absorbed by the fiber or cannulae as heat which can damage the probe or healthy tissue surrounding the probe.

FIG. 5a illustrates the paths of four distinct light rays identified as alpha ($\alpha$), beta ($\beta$), gamma ($\gamma$), and delta ($\delta$) being communicated by the fiber 40. Light ray alpha ($\alpha$) is shown travelling along the longitudinal axis 43 of the optical fiber 40. It is reflected at surface 42 causing it to contact an internal side of the transmitting surface 48 at an angle perpendicular to the surface of the transmitting surface 48. Accordingly, there is no second reflection of the light ray $\alpha$ as it travels straight through and out of an external side of the transmitting surface 48.

Light ray beta ($\beta$) is reflected off the bevelled surface 42 at a position closer to the interface 49, and therefore, does not contact the transmitting surface 48 at an angle perpendicular to the transmitting surface 48. As shown in FIG. 5a, the angle of incidence ($\theta_i\theta$), causes light ray $\beta$ to be bent at the transmitting surface 48 at an angle, but not internally reflected within the optical fiber 40. Light ray gamma ($\gamma$), which is closer to the interface 49 than light ray $\beta$, contacts the transmitting surface 48 at an angle of incidence which is greater than the critical angle, and therefore is internally reflected twice on the sides of the fiber, until it finally exits the fiber on the surface 42 at point 500. Finally, light ray $\delta$, which is being communicated at the extreme side of the core 44 and the closest of the illustrated waves to the interface 49, contacts the transmitting surface 48 at an angle of incidence less than the critical angle, and therefore is internally reflected within the optical fiber 40 twice on the sides, and exits the surface 42 at point 501. As a result, light rays $\gamma$ and $\delta$ are internally reflected off the surface 48 and incident on an opposing side of the surface 48 at incident angles greater than the critical angle, and therefore, are once again internally reflected within the optical fiber 40 as can be seen in FIG. 5a. This multiple internal reflection results in light rays $\gamma$ and $\delta$ exiting the optical fiber in undesired directions. FIG. 5b provides a perspective view of the resulting transmitted directions of light rays $\alpha$, $\beta$, $\gamma$ and $\delta$ using the same reference numbers as FIG. 5a.

FIG. 5c is an end view of the bevelled end 42 wherein a greater number and concentration of light ray paths are illustrated using the same reference numbers as FIG. 5a. FIG. 5c illustrates a computer generated model showing how only 72% of the light energy communicated by a conventional cylindrical fiber is directed in the desired directed indicated by arrow 502. Approximately 8% of communicated light energy is directed to the sides of the desired direction, and approximately 20% of the light energy is directed in a direction opposite the desired direction 49. As can be seen in this computer generated model, almost 30% of the communicated light energy in a conventional cylindrical fiber is directed in undesired directions.

FIGS. 6, 6a, and 6b are enlarged views of the optical fiber shown in FIGS. 1–4. The distal end or tip 51 of the optical fiber 23 (without cladding) includes a flat bevelled surface or end 24 having a bevel angle $\theta_B$ between a normal to the surface and the longitudinal axis 13 being greater than the critical angle ($\theta_B > \theta_C$). As shown more clearly in the side view of FIG. 6b, light rays communicated by the waveguide 23 along axis 13 will have an angle of incidence $\theta_I$ near $\theta_B$ and greater than the critical angle $\theta_C$, and are internally reflected by the bevelled end 24 in a direction toward the transmitting surface 25 in a direction (D).

The bevel angle $\theta_B$ varies based on the relative index of refraction of the surface 24 and the resulting critical angle. If the fiber 23 is made of quartz (which has an index of refraction of about 1.44) and is used in an ambient environment such as air ($N_{air} = 1.00$), total internal reflection occurs when the bevel angle $\theta_B$ is typically about 52°. An optical fiber having a higher index of refraction, such as 1.62, can also be used wherein $\theta_B$ could be about 45° in air. FIG. 1 illustrates the direction of laser energy 20 for a fiber having a bevel angle $\theta_B$ of about 52° which reflects light energy at less than a perpendicular angle relative to the probe 17. Using an optical fiber having a higher index of refraction enables $\theta_B$ to be about 45°, which enables light energy to be directed essentially perpendicular to the probe 17.

The optical fiber tip 23 includes two flat sides 36 that are on opposite sides of the transmitting surface 25 and parallel to the direction light rays are reflected by the reflecting surface 24. The direction of the electromagnetic radiation communicated by the waveguide 50 towards the tip 51 is a first primary direction which is shown by arrow 57, and the desired direction D is a second primary direction. The transmitting surface 25 is an arc positioned between the two opposing flat sides 36. The junction between the transmitting surface 25 and the two opposing flat sides 36 forms longitudinal edges 32. The fiber 23 can be formed by molding the shape of the fiber 23 or polishing down the two flat sides 36. The fiber tip 51 can be formed in the distal end of an optical fiber 23 as a unitary component or coupled to the distal end of another optical fiber serving as a waveguide using a transparent adhesive or otherwise. The index of refraction of the adhesive should match that of the tip 51 to prevent refraction or reflection of communicated light rays.

In order to clarify the relation between the reflecting surface 24 and the particular area 28 of the transmitting surface 25, light beam paths $\alpha$, $\beta$, $\gamma$, $\delta$ are shown in FIG. 6a. Light rays $\alpha$, $\beta$, $\gamma$, and $\delta$ do not strike the sides 36, and are all incident on the particular area 28 of the transmitting surface 25 at an angle that is less than the critical angle, thereby preventing internal reflection off the internal side of the transmitting surface 25 and enabling each of the light rays to be laterally directed in the desired direction (D). By omitting or "cutting off"

the extreme sides of a completely cylindrical fiber to form flat sides that are parallel to the desired direction (D) of transmission, light rays are communicated by the optical fiber 23 at positions adjacent to the extreme peripheral sides of the optical fiber 23 (the farthest distance from the longitudinal axis 13) and are reflected by the reflecting surface 24 so as to be incident on the particular are 28 of the transmitting surface 25 at an angle below the critical angle, thereby preventing internal reflection off the transmitting surface 25.

FIGS. 7 and 7a illustrate another embodiment of the present invention wherein an optical fiber 60 having a tip 68 is configured to have an extending rectangular cross-section taken perpendicular to a longitudinal axis 63. The optical fiber tip 68 includes a flat bevelled end 61 and a transmitting surface 62. The particular area 39 of the transmitting surface 62 is defined by dashed line 55 and longitudinal edges 56,47,58. The bevelled end 61 establishes an angle $\theta_B$ between a normal to the surface and longitudinal axis 63, wherein angle $\theta_B$ is above the critical angle in order to have complete internal reflection of light rays off the reflecting surface 61.

A first flat side 59 of the rectangular tip 61 includes the transmitting surface 62. Two additional, parallel flat sides 66 of the rectangular tip intersect the first flat side 59. The junctions between the two flat sides 66 and the flat side 59 form the longitudinal edges 56 and 58. The bottom flat side 67 of the rectangular tip 61 is opposite and parallel to the first flat side 59. The bevelled end 61 has four longitudinal edges 57. The two flat sides 66 and the bottom flat side 67 intersect to form longitudinal edges 47.

The fiber tip 61 is preferably formed by extruding the rectangular configuration or polishing flat the sides on a conventional cylindrical fiber. The tip 61 can be formed into the distal end of an optical fiber or coupled to the distal end of the optical fiber with a transparent adhesive index matched with the waveguide and the tip.

FIG. 7a illustrates how all of the light rays $\alpha$, $\beta$, $\gamma$, and $\delta$ do not strike the sides 66 and are incident on the particular area 39 of the transmitting surface 62 at a perpendicular angle, thereby passing directly through and out the transmitting surface 62 in the desired direction D. As can be seen in FIG. 7a, the purpose of the present invention is achieved by the illustrated configuration by preventing reflected light rays from being incident on the transmitting surface 62 at an incident angle below the critical angle in order to prevent internal reflection off the transmitting surface 62.

In order to emphasize the variety of possible embodiments that may be utilized to achieve the present invention, FIGS. 8 and 8a are also provided to illustrate a further possible embodiment configured in accordance with the present invention. The optical fiber 70 has a triangular cross-section taken perpendicular to an longitudinal axis 73. The triangular cross section extends to the flat bevelled end or internally reflecting surface 72. A first side 74 forms the transmitting surface, and the particular area 77 is defined by the dash line reference line 71 and longitudinal edges 76 and 78. Longitudinal edges 76A and 76B are formed by the junctions between the flat sides 74,75,79. Longitudinal edges 78 are formed at junctions between the bevelled end 72 and the flat surfaces 74,75,79. Similar to the previous embodiments, the bevel angle $\theta_B$ of the normal to the bevelled end 72 with respect to an longitudinal axis 73 of the optical fiber tip 71 is above the critical angle in order to have total internal reflection of light rays being communicated toward the reflecting surface 72. Again, rays $\alpha$, $\beta$, $\gamma$, and $\delta$ do not strike sides 75, 79 and are incident on the surface 74 at below the critical angle.

The fiber 70 can be manufactured by extruding optical fiber material or polishing a standard optical fiber into the illustrated triangular configuration. The fiber 70 can be formed into the waveguide or attached to the distal end of an optical fiber or waveguide using transparent, index matched adhesive.

As with the previously illustrated embodiments of the present invention, the particular area 77 of the transmitting surface 74 must be disposed relative to the reflecting surface 72 such that substantially all light rays reflected by the reflecting surface are incident on the particular area 77 below the critical angle in order to prevent internal reflection off the internal side of the transmitting surface 74. Since the surface of the particular area 77 is perpendicular to the light ray paths of the light rays reflected by the reflecting surface 72, all reflected light are incident on the particular area 77 below the critical angle, and thus, pass directly through the transmitting surface 74.

Figure 9:
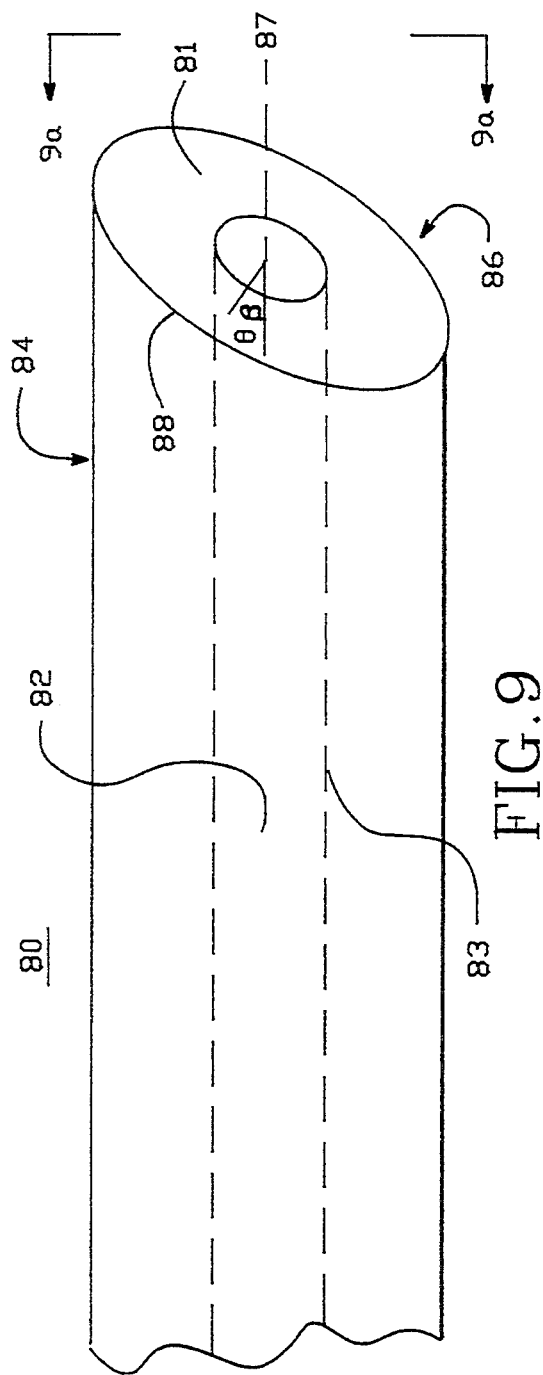
FIG. 9 is a perspective view of an optical fiber tip configured in accordance with a further embodiment of the present invention.
Figure 9A:
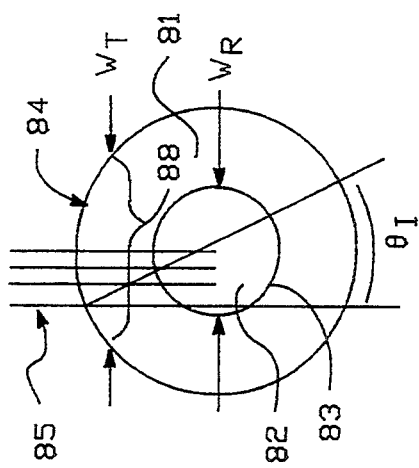
FIG. 9a is an end view of the fiber tip taken along line 9a–9a of FIG. 9.

FIGS. 9 and 9a illustrates another possible configuration for achieving the present invention wherein the diameter of core cladding layer 81 surrounding a fiber optic core 82 is increased so that light rays 85 traveling adjacent to a perimeter 83 of the fiber optic core 82 are incident on the particular area 88 of the transmitting surface 84 at an angle less than the critical angle in order to preventing internal reflection off the internal side of the transmitting surface 84. In this embodiment, the index of the core cladding layer 81, and the index of the fiber optic core are quite similar which results in only slight refraction when light rays 85 pass between the perimeter or interface 83 between the fiber core 82 and the core cladding layer 81. Typically, the index of refraction is 1.45 for a fiber core, 1.43 for cladding, and 1.00 for air. Using a quartz tip in air, the angle between the bevelled surface and the fiber axis ($90-\theta_B$) is preferably 38°.

Similar to other embodiments, the tip 80 includes a flat bevelled end 86 that has bevel angle $\theta_B$ with respect to an longitudinal axis 87 above the critical angle to provide complete internal reflection. The core cladding layer 81 is constructed of glass and positioned around the fiber core 82 using conventional manufacturing procedures. The "cladding" of a typical fiber optic includes an additional hard plastic cladding layer (not shown) which lies over the core cladding layer 81. The additional hard plastic cladding layer is used in case the fiber is bent so that the core cladding layer 81 suffers leakage due to increased incidence angles in the bent portion. Over the hard plastic cladding, a nylon jacket is applied to protect the hard plastic from scratching or other damage. The jacket and hard plastic cladding layer are stripped back away from the tip in this embodiment.

The necessary relation of the invention between the reflecting surface 86 and the particular area 88 is achieved by the increased thickness of the core cladding layer 81. As the thickness of the core cladding layer 81 relative the core 82 increases, the curvature of the surface of the cladding 81 per unit width, and thus the transmitting surface 84, decreases. The decreased curvature of the transmitting surface 84 results in all or substantially all of light rays reflected by the reflecting surface being incident on the particular area 88 of the transmitting surface with an angle of incidence $\theta_I$ less than or equal to the critical angle.

It can be seen in FIGS. 6a, 7a, 8a and 9a that the reflecting surfaces have a width $W_R$ transverse to the lateral direction that is less than or equal to the width $W_T$ of the area on the transmitting surface in which light propagating in the lateral direction is incident at below the critical angle.

Figure 10:
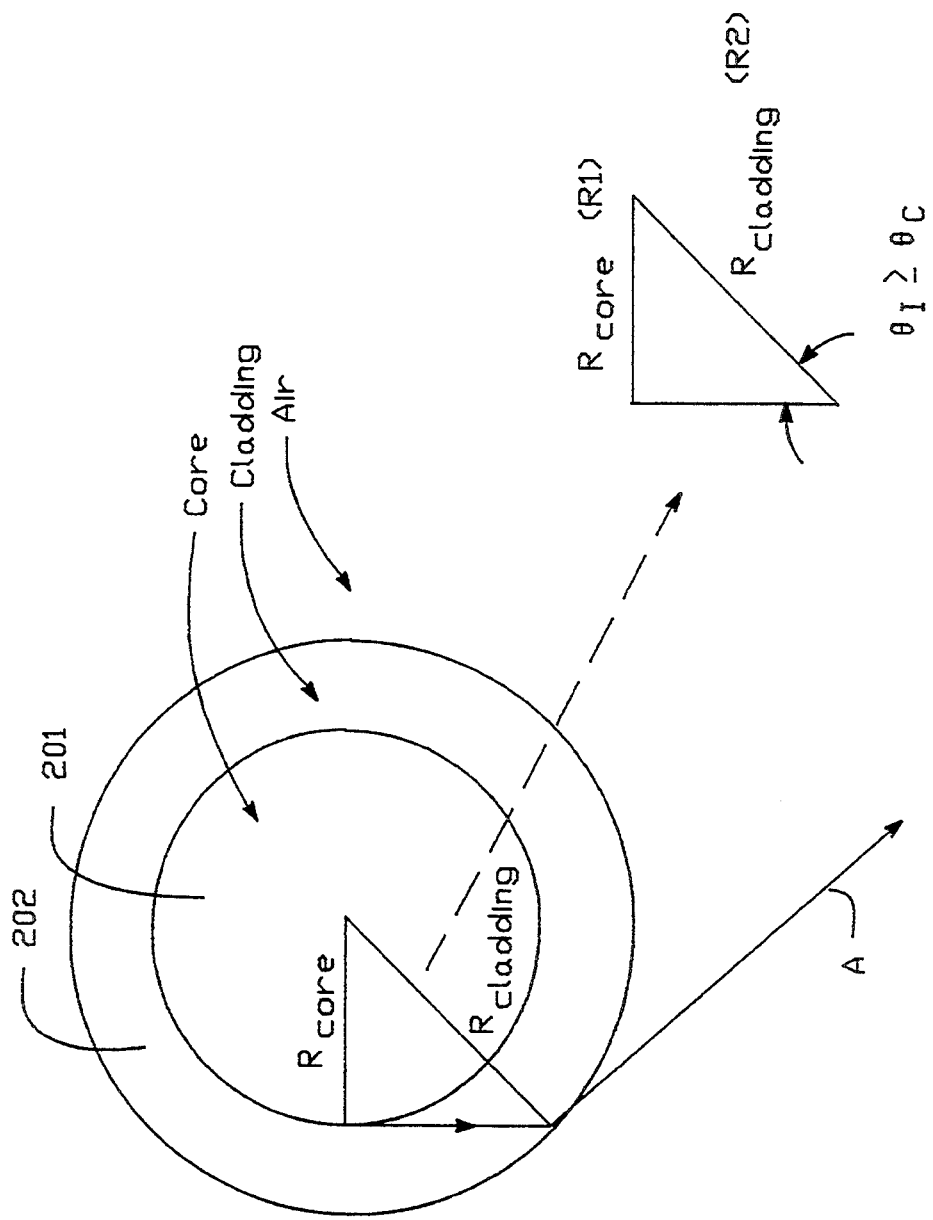
FIG. 10 is a diagram used for determining the necessary requirements for an optical fiber and surrounding cladding so as to be constructed in accordance the present invention.

FIG. 10 provides a diagram and method for determining the required core cladding-to-core diameter ratio of the embodiment illustrated in FIGS. 9 and 9a. The drawing illustrates a cross-sectional or end view of a bevelled optical fiber core 201 including cladding 202. A "worst case" ray of light (A) is being communicated at the extreme side of the core 201 ignoring the slight refraction losses at the cladding-core interface.

As shown in the diagram:
Root$_{core}$=radius of the core
R$_{cladding}$=radius of the core cladding layer from the center of the fiber core
N$_{air}$=index of refraction for air
N$_{cladding}$=index of refraction for the core cladding
k=core-to-core cladding radius ratio; 1/k=core cladding-to-core radius ratio
$\theta_C$=critical angle
sin $\theta_C$=N$_{air}$/N$_{cladding}$
sin $\theta_C$=R$_{core}$/R$_{cladding}$
sin $\theta_C$=(k.R$_{cladding}$)/R$_{cladding}$
sin $\theta_C$=k Therefore, in a typical fiber with N$_{cladding}$=1.433 and N$_{air}$=1.00:
critical angle $\theta_C$=44.25°
core-to-core cladding radius ratio k=0.7
1/k=1.43

This embodiment of the present invention achieves substantially improved performance of the lateral directing fiber probe, with a relatively inexpensive structure. Experimental results establish that substantially all of the laser energy transmitted through the fiber can be laterally directed by the probe in the direction desired.

An outline of the comparative experimental results is provided below. There were two experiments and the procedures are described here:
First Experiment (1/k=1.4)
Materials:
400/560/585/750 micron fiber made out of pure fused silica core/doped fused silica or glass core cladding/hard plastic buffer cladding layer/nylon jacket. Ensign-Bickford Optics Company part number which has a 1.4 clad/core ratio is PB03978, and the equivalent 3M Optics Company version is CS-92-4702.

Fused quartz cap made from tubing 590 micron inner diameter, 825 micron outer diameter, and 15±/0.1 mm in length, closed at one end and open at the other.
Dymax 128-M ultra-violet curable adhesive
Helium neon laser
United Detector Technologies UDT-371 optical power meter Procedure:

The 1.4, glass cladding-to-fused silica core ratio, fiber was beveled to 38 degrees±/1 degree ($\theta_B$=52°±1°) and stripped down to the glass cladding a length of 12±1 mm from the centerline of the bevel. The quartz cap was bonded onto the beveled and stripped fiber with the Dymax 128-M adhesive with a bond seal length of 2 to 6.35 mm from the open end of the cap (no adhesive was allowed within 5 mm of the bevel location). A helium neon laser beam was focused into the proximal end of the fiber and the side firing beam in the intended direction was reflected from the bevel consisted of ~80% of the incident light into the fiber as measured with the UDT optical power meter. Only about 5% was directed in the opposite direction of the intentional side firing beam in a fan-like distribution and orthogonal to the fiber axis. Thus, of the 85% of the input energy which was detected on transmission out of the fiber, greater than 90% (about 94%) of the energy was transmitted through the upper surface of the cladding layer, without undesirable deflection.

Second Experiment (1/k=1.1)
Materials:
400/440/470 micro fiber made out of pure fused silica core/doped fused silica or class cladding/polyimide jacket (no buffer).

Fused quartz cap made from tubing 500 micron inner diameter, 825 micron outer diameter, and 15.2±/0.1 mm in length, closed at one end and open at the other.
Dymax 128-M ultra-violet curable adhesive
Procedure:

The 1.1 clad-to-core ratio fiber supplied was assembled with the quartz cap already bonded to the beveled and stripped fiber, similar to that described above. The same helium neon laser beam was focused into the proximal end of the fiber and the side firing beam which was intentionally reflected from the bevel consisted of ~70% of the incident light into the fiber as measured with the UDT optical power meter. About 15% of the input energy was directed in the opposite direction of the intentional side firing beam in a fan-like distribution and orthogonal to the fiber axis.
Result:

The result of using a clad-to-core ratio of 1.4 (the first experiment) decreases unintentionally directed laser light from 15% to 5% with a corresponding increase in energy of the main side firing beam. This will prevent unintentional laser damage to tissue or to a cannula that is in close proximity to the fiber/quartz cap assembly, particularly at the opposite side of the assembly that the main side firing beam is directed.

In a finished product, a cannula is attached around the fiber assembly where a window is cut out of the side of it and the intended or main, side firing beam emanates. The change of the fiber from a 1.1 to 1.4 clad-to-core ratio has resulted in significantly longer usage of the device before the cannula becomes damaged by the unintentionally directed laser energy. Even better performance is expected with higher clad-to-core ratios for a given material.

While a fiber optic tip constructed in accordance with the present invention can be formed into the distal end of a waveguide, the tip of the present invention can be a separate component that is coupled to the distal end of a waveguide using transparent adhesive index matched to the waveguide. Furthermore, the tip can have a different cross-sectional configuration than the waveguide to which it is coupled and still function in accordance with the present invention.

FIG. 11 illustrates such an embodiment wherein a rectangular tip 90 is coupled to a cylindrical optical fiber 92 in accordance with the present invention. The tip 90 is illustrated in FIGS. 11 and 11a as having a larger width than the fiber core 92, however, the tip 90 can a width equal to the fiber core 92 and still function in accordance with the invention. A proximal end 91 of the tip 90 is secured to a distal end of the fiber core 92 by fusing or by using a transparent adhesive 94 that is index matched with the fiber 92 and the tip 90 in order to prevent reflection or refraction at the interface between fiber 92 and the adhesive 94, or the tip 90 and the adhesive 94.

The tip 90 includes a flat bevelled end 95 with bevel angle $\theta_B$ greater than $\theta_C$, and a transmitting surface 97 on one side of the rectangular tip 90. Although it is not necessary as long as the angle of the bevelled end 95 is greater than the critical angle, a reflective coating 99 can be included on the reflecting surface 95. Light ray paths 98 are included in end view 11a to illustrate that the particular area 111 of the transmitting surface 97 is disposed such that light rays reflected by the bevelled end 95 are incident on the particular area 111 below the critical angle in accordance with the present invention.

FIG. 12 illustrates a further embodiment of the present invention wherein a first end 103 of a transparent tube 100 having a hollow inside 109 is secured to a distal end 101 of an optical fiber or waveguide 102 having a bevelled end 106. The second end 110 of the tube 100 is hermetically sealed with a plug 104, thus creating a sealed cavity 105 within the tube 100. The cavity 105 contains a predetermined medium, such as air, to obtain a desired ratio of refraction indices between the bevelled end 106 and the medium within the cavity 105.

The tube 100 is secured to the fiber 102 using a transparent adhesive 108 applied around a periphery of the distal end 101 of the fiber 102. This transparent adhesive 108 extends to the edges of the bevelled end 106, but not onto the surface of the bevelled face 106. The adhesive 108 and the tube 100 are preferably index matched with the fiber 102 to prevent undesired internal reflections of electromagnetic radiation being reflected by the bevelled end 106 and passing through the adhesive 108 and the tube 100 and out the transmitting surface 107 on the surface of the tube 100. The plug 104 can be composed of a flexible material, such as rubber.

The present invention can be adapted to tools with other uses besides urology, such as procedures in the fields of neurology, otorhinolaryngology, general anesthetic ophthalmology, dentistry, gastroenterology, cardiology, and gynecology. Thoracic and orthopedic procedures may also be improved according to the present invention. For instance, a tool including the laterally directing tip of the present invention can be utilized in any number of surgical procedures, such as percutaneous ablation of an intrapelvic renal tumor, or percutaneous incision of an ureteropelvic junction obstruction.

More particularly, because the present invention provides a system for laterally delivering laser energy with precisely controlled dosage and very little waste heat, this type of technology can be applied to numerous medical procedures not available in the prior art.

In the field of neurology, endoscopic surgery for shunt revision or shunt removal can be accomplished. This procedure would involve inserting a fiber having a laterally directing tip, as described above, into position using an endoscope with a 4 mm outside diameter, with direct visualization or video visualization for assistance. Critical working conditions of this type of environment require systems, such as the present invention, for precisely controlled delivery of energy.

A probe, according to the present mention, may also be used in ventriculocystomy, third ventriculostomy, tumor biopsy and resection, transeptal and transaquaductal membrane fenestration, removal of proximal ventricular catheters or shunts, and decompression of hydromyelia and intraspinal arachnid cysts.

In the field of cardiology, probes, according to the present mention, may be used for coronary bypass surgery, removal of atherosclerotic plaque from coronary arteries and endarterectomy. All of these procedures can be performed utilizing specific endoscopes, with direct visualization or video assistance.

The system may also be employed with cardiac windows, adhesions, tumors, lesions and cysts in endoscopic procedures or open procedures.

In the field of gynecology, probes, according to the present mention, may be used for endometrial ablations, uterine septums, uterine myomata inside the uterus using hysteroscopically or laparoscopically delivered probes. The probe may also be applied laparoscopically for the removal of endometrial implants used to treat endometriosis, removal of ovarian cysts, removal of fibroids, removal of pelvic adhesions, laparoscopic uterosacral nerve ablation, and for laser assisted hysterectomy.

The probe can be applied in laparoscopic cholecystectomy, abdominal and pelvic adhesion procedures, treatment of hernias, appendectomies, enterolysis and esophagoscopy.

Orthopedic procedures to which the present invention is suitable include arthroscopic chondromalacia, and laser disc decompression procedures.

In the ear, nose, and throat field, the probe, according to present mention, can be used to treat laryngeal lesions, particularly on the vocal chords, for turbinectomies in the sinuses and for bronchoscopy.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus for communicating and laterally directing electromagnetic radiation, comprising:
   a waveguide having a tip for communicating electromagnetic radiation in a propagation direction to the tip of the waveguide;
   a transmitting surface on the tip of the waveguide;
   a reflecting surface on the tip of the waveguide for internally reflecting electromagnetic radiation communicated by the waveguide in a direction lateral to the propagation direction toward a particular area on the transmitting surface; and
   wherein the particular area and the reflecting surface are disposed so that greater than about 90% of electromagnetic radiation reflected by the reflecting surface is incident on the particular area at below a critical angle for transmission through the transmitting surface in the lateral direction.

2. The apparatus of claim 1, wherein the tip of the waveguide comprises a fiber optic segment, the fiber optic segment including a fiber core having an outside radius R1 and a core cladding having an outside radius R2 and a cylindrical outside surface, wherein R2 is equal to greater than about 1.4 times R1; and wherein the reflecting surface comprises a bevelled surface on the fiber core at a distal end of the tip and the transmitting surface comprises a portion of the cylindrical outside surface of the core cladding.

3. The apparatus of claim 2, wherein the fiber core comprises fused quartz, and the core cladding comprises doped fused quartz.

4. The apparatus of claim 1, wherein the tip of the waveguide comprises a fiber optic segment, the fiber optic segment including a fiber core having an outside radius R1, a bevelled end surface, and an index of refraction N1, and a core cladding having an outside radius R2, an index of refraction N2 and a cylindrical outside surface, wherein the reflecting surface comprises an interface between an external medium and the bevelled end surface on the fiber core at a distal end of the tip and the transmitting surface comprises a portion of the cylindrical outside surface of the core cladding, the external medium having index of refraction NA, and wherein R2/R1 is greater than or equal to about N2/NA.

5. An apparatus for communicating and laterally directing electromagnetic radiation, comprising:
- a waveguide core having a cylindrical peripheral surface with radius R1, and comprising a transmissive material having a first index of refraction, through which electromagnetic radiation is transmitted in a propagation direction;
- a bevelled tip on the waveguide core to reflect electromagnetic radiation transmitted through the waveguide core in a lateral direction relative to the propagation directions through the core;
- core cladding comprising a transmissive material having a second index of refraction sightly less than the first index of refraction, disposed on the peripheral surface of the waveguide core at least in a region near the bevelled tip through which electromagnetic radiation propagating in the lateral direction from the bevelled tip is transmitted, and having a cylindrical outside surface in said region with radius R2 exposed to a medium having a third index of refraction less than the second index of refraction;
- wherein R1 is essentially k times R2, and k is less than or equal to the third index of refraction divided by the second index of refraction.

6. The apparatus of claim 5, wherein the waveguide core comprises fused quartz, the core cladding comprises doped fused quartz.

7. An apparatus for communicating and laterally directing electromagnetic radiation, comprising:
- a waveguide having a tip for communicating electromagnetic radiation in a propagation direction to the tip of the waveguide;
- a reflecting surface on the tip of the waveguide for internally reflecting electromagnetic radiation communicated in the propagation direction by the waveguide in a lateral direction relative to the propagation direction;
- a transmitting surface on the tip of the waveguide having a particular area within which radiation propagating in the lateral direction is incident at below a critical angle for transmission through the transmitting surface, wherein at least 90% of all electromagnetic radiation reflected by the reflecting surface;

said reflecting surface and said particular area having first and second widths that both extend to the reflecting surface, respectively, transverse to the propagation direction, and wherein the second width is at least 1.4× greater than the first width.

8. The apparatus of claim 7, wherein the reflecting surface comprises a bevelled surface at a distal end of the tip.

9. The apparatus of claim 8, wherein the tip comprises quartz and the bevelled surface is disposed at an angle of about thirty-eight (38) degrees relative to the propagation direction.

10. The apparatus of claim 8, wherein the tip has two opposing sides in respective planes parallel to the lateral direction such that the particular area is limited by an intersection of the two opposing sides and the bevelled surface with the transmitting surface.

11. The apparatus of claim 10, wherein the transmitting surface has a cylindrical curve and the two opposing sides intersect the cylindrical curve at below a critical angle.

12. The apparatus of claim 10, wherein the transmitting surface is essentially flat.

13. The apparatus of claim 8, wherein the tip has sides intersecting the transmitting surface and extending to the bevelled surface to define a shape of the reflecting surface so that electromagnetic radiation reflected by the reflecting surface does not strike the sides.

14. The apparatus of claim 13, wherein the tip has a triangular cross-section.

15. The apparatus of claim 13, wherein the tip has a rectangular cross-section.

16. The apparatus of claim 8, wherein the waveguide comprises an optical fiber.

17. The apparatus of claim 16, wherein the optical fiber has a relatively high index of refraction of about 1.62, and the bevelled surface is disposed at an angle of about 45 degrees relative to the propagation direction.

18. The apparatus of claim 7, further comprising:
- a tube with a hollow inside having a first end secured to the tip and enclosing the reflecting surface and the transmitting surface, the hollow inside of the tube positioned against and forming a cavity adjacent to the reflecting surface, and a second end of the tube having a plug for maintaining a selected medium within the cavity adjacent to the reflecting surface.

19. The apparatus of claim 7, further comprising:
- a transparent cap secured to the waveguide and enclosing the reflecting surface on the tip, the transparent cap turning an angle of the reflect electromagnetic radiation from the lateral direction.

20. The apparatus of claim 7, further comprising:
- a transparent cap, secured to the tip and enclosing the reflecting surface and the transmitting surface, forming a sealed cavity adjacent to the reflecting surface for maintaining a selected medium within the cavity adjacent to the reflecting surface.

21. The apparatus of claim 7, wherein the tip of the waveguide comprises a fiber optic segment, the fiber optic segment including a fiber core having an outside radius R1, a bevelled end surface, and an index of refraction N1, and a core cladding having an outside radius R2, an index of refraction N2 and a cylindrical outside surface, wherein the reflecting surface comprises an interface between an external medium and the bevelled end surface on the fiber core at a distal end of the tip and the transmitting surface comprises a portion of the cylindrical outside surface of the core cladding, the external medium, having index of refraction NA, and wherein R2/R1 is greater than or equal to about N2/NA.

22. The apparatus of claim 7, wherein at least the tip of the waveguide comprises an optical fiber having a fiber core with a radius $R_1$, and transmissive core cladding on the fiber core with an outside surface defining a critical angle between the core cladding and an outside medium and a radius $R_2$, and wherein the radius $R_2$ is equal to or greater than about $R_1$ divided by sine of the critical angle between the core cladding and the outside medium.

23. The apparatus of claim 7, wherein the tip of the waveguide comprises a fiber optic segment, the fiber optic segment including a fiber core having an outside radius R1 and a core cladding having an outside radius R2 and a cylindrical outside surface, wherein R2 is equal to greater than about 1.4 times R1; and wherein the reflecting surface comprises a bevelled surface on the fiber core at a distal end of the tip and the transmitting surface comprises a portion of the cylindrical outside surface of the core cladding.

24. The apparatus of claim 23, wherein the fiber core comprises fused quartz, and the core cladding comprises doped fused quartz.

25. A surgical probe for treating benign prostatic hyperplasia (BPH), said probe, comprising:
a waveguide having a tip with a glass cladding extending to a distal end of the tip, the waveguide for communicating electromagnetic radiation in a first propagation direction to the tip of the waveguide;
means for positioning the waveguide during surgery;
a transmitting surface on the tip of the waveguide;
a reflecting surface on the tip of the waveguide for internally reflecting electromagnetic radiation communicated in the first propagation direction by the waveguide in a second propagation direction toward the transmitting surface; and
wherein at least 90% of all electromagnetic radiation reflected by the reflecting surface is incident on the transmitting surface at below a critical angle for transmission through the transmitting surface.

26. The apparatus of claim 25, wherein the tip of the waveguide comprises a fiber optic segment, the fiber optic segment including a fiber core having an outside radius R1, a bevelled end surface, and an index of refraction N1, and a core cladding having an outside radius R2, an index of refraction N2 and a cylindrical outside surface, wherein the reflecting surface comprises an interface between an external medium and the bevelled end surface on the fiber core at a distal end of the tip and the transmitting surface comprises a portion of the cylindrical outside surface of the core cladding, the external medium having index of refraction NA, and wherein R2/R1 is greater than or equal to about N2/NA.

27. The apparatus of claim 25, wherein the means for positioning the waveguide includes a tube having a hollow passage, and the waveguide is positioned within the hollow passage.

28. The apparatus of claim 27, wherein the tube comprises a rigid cannula.

29. The apparatus of claim 27, wherein the tube comprises a flexible catheter.

30. The apparatus of claim 25, wherein the reflecting surface comprises a bevelled surface at the distal end of the tip.

31. The apparatus of claim 30, wherein the tip has two opposing sides in respective planes parallel to the second propagation direction so that the reflecting surface is limited by an intersection of the two opposing sides and the bevelled surface.

32. The apparatus of claim 30, wherein the tip has sides intersecting the transmitting surface and extending to the bevelled surface to define a shape of the reflecting surface so that electromagnetic radiation reflected by the reflecting surface does not strike the sides.

33. The apparatus of claim 25, wherein the tip of the waveguide comprises a fiber optic segment, the fiber optic segment including a fiber core having an outside radius R1 and a core cladding having an outside radius R2 and a cylindrical outside surface, wherein R2 is equal to greater than about 1.4 times R1; and wherein the reflecting surface comprises a bevelled surface on the fiber core at a distal end of the tip and the transmitting surface comprises a portion of the cylindrical outside surface of the core cladding.

34. The apparatus of claim 33, wherein the fiber core comprises fused quartz, and the core cladding comprises doped fused quartz.

* * * * *

(12) EX PARTE REEXAMINATION CERTIFICATE (8132nd)
United States Patent
Pon

(10) Number: US 5,428,699 C1
(45) Certificate Issued: Apr. 5, 2011

(54) PROBE HAVING OPTICAL FIBER FOR LATERALLY DIRECTING LASER BEAM

(75) Inventor: Russell Pon, Santa Clara, CA (US)

(73) Assignee: Laserscope, San Jose, CA (US)

Reexamination Request:
No. 90/010,479, Mar. 30, 2009

Reexamination Certificate for:
Patent No.: 5,428,699
Issued: Jun. 27, 1995
Appl. No.: 08/086,014
Filed: Jul. 2, 1993

(51) Int. Cl.
 G02B 6/26 (2006.01)

(52) U.S. Cl. .................. 385/31; 385/39; 385/47; 385/901; 600/108; 606/7
(58) Field of Classification Search .......... None
See application file for complete search history.

(56) References Cited

U.S. PATENT DOCUMENTS

| | | |
|---|---|---|
| 4,092,061 A | 5/1978 | Stigliani, Jr. |
| 4,165,152 A | 8/1979 | Shiraishi et al. |
| 4,165,915 A | 8/1979 | Rau et al. |
| 4,221,825 A | 9/1980 | Guerder et al. |
| 4,273,127 A | 6/1981 | Auth et al. |
| 4,435,040 A | 3/1984 | Cohen et al. |
| 4,445,892 A | 5/1984 | Hussein et al. |
| 4,566,438 A | 1/1986 | Liese et al. |
| 4,620,547 A | 11/1986 | Boebel |
| 4,669,467 A | 6/1987 | Willett et al. |
| 4,691,991 A | 9/1987 | Unger |
| 4,740,047 A | 4/1988 | Abe et al. |
| 4,819,632 A | 4/1989 | Davies |
| 4,832,979 A | 5/1989 | Hishino |
| 4,852,567 A | 8/1989 | Sinofsky |
| 5,000,752 A | 3/1991 | Hoskin et al. |
| 5,005,180 A | 4/1991 | Edelman et al. |
| 5,041,121 A | 8/1991 | Wondrazek et al. |
| 5,061,265 A | 10/1991 | Abela et al. |
| 5,093,877 A | 3/1992 | Aita et al. |

(Continued)

FOREIGN PATENT DOCUMENTS

| | | |
|---|---|---|
| EP | 0163266 | 12/1985 |
| EP | 0177928 | 4/1986 |
| EP | 0324844 | 7/1989 |
| JP | 61219904 | 9/1986 |
| JP | 61-219904 | 9/1986 |
| JP | 3-63377 | 3/1991 |
| JP | 363377 | 9/1991 |
| JP | 2146485 | 10/1992 |

OTHER PUBLICATIONS

Helium–Neon Laser Heads 1100 Series Product Brochure, Rev. 5, dated Jan. 2006. (Exhibit M to Declaration of Scott McBride in Support of Plaintiffs' Motion to Exclude Testimony of Dr. Wayne Knox, dated Mar. 13, 2010).

(Continued)

Primary Examiner—Minh T Nguyen

(57) ABSTRACT

An improved optical fiber for laterally directing a laser beam having a waveguide including a tip for communicating electromagnetic radiation in a propagation direction to the tip of the waveguide, a transmitting surface on the tip of the waveguide, a reflecting surface on the tip of the waveguide for internally reflecting electromagnetic radiation communicated by the waveguide in a direction lateral to the propagation direction toward a particular area on the transmitting surface, and wherein the particular area and the reflecting surface are disposed so that substantially all electromagnetic radiation reflected by the reflecting surface is incident on the particular area at below a critical angle for transmission through the transmitting surface in the lateral direction. By preventing electromagnetic radiation from being incident on the transmitting surface above a critical angle, the present invention prevents internal reflection off the transmitting surface and improves the efficiency of the laterally directing probe.

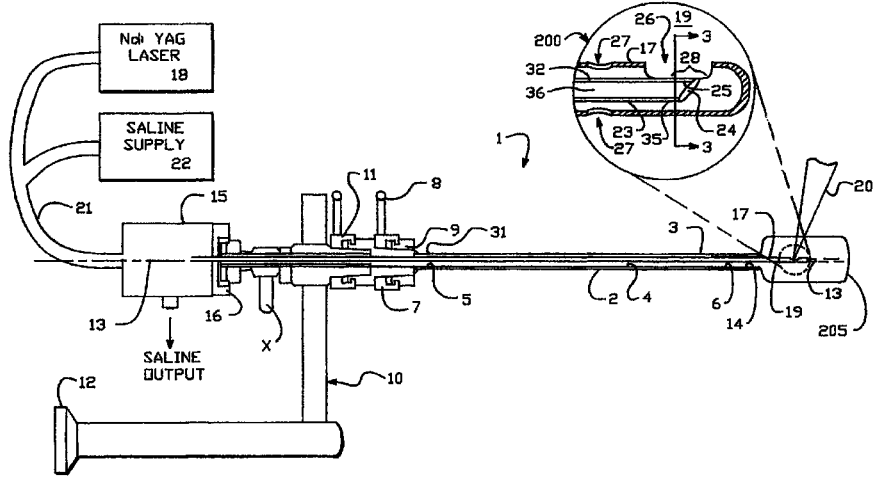

U.S. PATENT DOCUMENTS

| | | | |
|---|---|---|---|
| 5,253,312 | A | 10/1993 | Payne et al. |
| 5,254,114 | A | 10/1993 | Reed, Jr. et al. |
| 5,275,991 | A | 1/1994 | Buehler et al. |
| 5,292,320 | A | 3/1994 | Brown et al. |
| 5,343,543 | A | 8/1994 | Novak, Jr. et al. |
| 5,354,294 | A | 10/1994 | Chou |
| 5,428,699 | A | 6/1995 | Pon |
| 5,498,260 | A | 3/1996 | Rink et al. |
| 5,537,499 | A | 7/1996 | Brekke |
| 5,562,657 | A | 10/1996 | Griffin |
| 5,807,389 | A | 9/1998 | Gardetto |
| 6,986,764 | B2 | 1/2006 | Davenport et al. |
| 7,447,409 | B2 | 11/2008 | Griffin |

OTHER PUBLICATIONS

Photograph of the 1100 Series Laser (Exhibit N to Declaration of Scott McBride in Support of Plaintiffs' Motion to Exclude Testimony of Dr. Wayne Know, dated Mar. 13, 2010).

Product Details for Optical Power Meter Model 371 (Exhibit 56 to Declaration of Scott McBride in Support for Plaintiffs' Opposition to Defendant's Motions for Summary Judgment of Invalidity and Noninfringement, dated Mar. 27, 2010).

Article entitled "UDT Instruments: The Guide to Radiometry" (Exhibit D to Declaration of Matthew Kellam in Support of Defendant's Reponse to Plaintiffs' Motion for Partial Summary Judgment, dated Mar. 29, 2010).

J.W. Fleming and D.L. Wood, Refractive Index Dispersion And Related Properties in Fluorine Doped Silica, Applied Optics vol. 22, No. 19 (Oct. 1, 1983).

Declaration of Matthew Kellam in Support of Defendant's Response to Plaintiffs' Motion for Partial Summary Judgment, dated Mar. 29, 2010.

Plaintiffs' Reply in Support of Motion for Partial Summary Judgment, dated Apr. 3, 2010.

Declaration of Scott McBride in Support of Plaintiffs' Reply Memorandum in Support of Plaintiffs' Motion for Partial Summary Judgment, dated Apr. 3, 2010.

Declaration of Matthew Kellam in Support of Defendant's Various Motions for Summary Judgment and Motions to Exclude Testimony, dated Mar. 12, 2010.

Memorandum in Opposition to Defendant's Motion for Summary Judgment of Invalidity, dated Mar. 27, 2010.

Declaration of Scott McBride in Support of Plaintiffs' Opposition to Defendant's Motions for Summary Judgment of Invalidity and Noninfringement, dated Mar. 27, 2010.

Defendant's Reply Memo in Support of Motion for Summary Judgment of Invalidity, dated Apr. 3, 2010.

AMS's Summary Judgment Presentation: Dispositive Motion Hearing, *American Medical Systems, Inc. et al.* v. *Laser Peripherals, LLC*, Case No. 08–04798, Apr. 15, 2010.

Transcript of Motions Hearing Before the Honorable Joan Ericksen, United States District Court Judge, District of Minnesota, Apr. 15, 2010.

Order of the Honorable Joan Ericksen, United States District Court Judge, District of Minnesota, May 13, 2010.

Memorandum in Support of Plaintiffs' Motion to Exclude Testimony of Dr. Wayne Knox, dated Mar. 13, 2010.

Brian P. McCann, Fiber Holds the Key to Medical Lasers' Success, Photonics Spectra, 127–132 (May 1990).

Brian P. McCann, Comparison of Silica–Core Optical Fibers, Optical Fibers in Medicine VI, SPIE vol. 1420, 116–125 (1991).

Hashimoto, D., et al., "Tip Prasmatic Lateral Probe for Nd–Yag Laser Radiation Therapy," Journal of Japan Laser Processing Society, vol. 6, No. 3 (Jan. 1986) pp. 487–489.

Daimon, M., et al., "Measurement of The Refractive Index of Distilled Water From The Near–infrared Region To The Ultraviolet Region," Applied Optics, vol. 46, No. 18 (Jun. 20, 2007) pp. 3811–3820.

Fresnel Equations, http://en.wikipedia.org/wiki/Fresnel_equations, dated Jan. 21, 2010.

Steeger, P., et al., "Polarization Preservation in Circular Multimode Optical Fibers and its Measurement by a Speckle Method," Journal of Lightwave Technology, vol. LT–2, No. 4 (Aug. 1984) pp. 435–441.

Sakai, Paulo, et al., "Gastrointestinal Endoscopy", Official Journal of the American Society for Gastrointestinal Endoscopy, Program Abstracts, vol. 32, No. 2, pp. 124–125, dated Apr. 1986.

Hashimoto, D., et al., "A Lateral Radiation Probe in YAG Laser Therapy," Gastrointestinal Endoscopy, vol. 32, No. 2, pp. 124–125, 1986.

Goldenberg, Tsvi, et al., "Laser Delivery Systems," Lasers in Cardiovascular Disease, pp. 42–56, (Rodney A. White et al., eds., 2d ed.), 1989.

Laudenslager, James B., "Laser Fundamentals, " Lasers in Cardiovascular Disease, pp. 10–31, (Rodney A. White et al., eds., 2d 3d.), 1989.

Isner, Jeffrey M., "Fibers," Cardiovascular Laser Therapy, pp. 17–38, (Jeffrey M. Isner et al. eds.), 1989Isner, Jeffrey M., "Fibers," Cardiovascular Laser Therapy, pp. 17–38, (Jeffrey M. Isner et al. eds.), 1989.

Keiser, G., "Optical Fiber Communications," pp. 26–28; pp. 114–117, McGraw–Hill, 2d. ed., 1983.

Costello, A.J., et al., "Laser Ablation of the Prostate in Patients with Benign Prostatic Hypertrophy", British Journal of Urology, vol. 69, pp. 603–608, 1992.

Augerson, C. C., et al., "Controlling the Refractive Index of Epoxy Adhesives with Acceptable Yellowing After Aging," Journal of the American Institute for Conservation, JAIC, vol. 32, No. 3, Article 8, pp. 311–314, http://aic.stanford.edu/jaic/articles/jaic32-03-008.html, 1993.

Childs, Stacy, J., "Laser Assisted Transurethral Resection of the Prostate," (Williams & Wilkins), 1993.

Verdaasdonk, Rudolph, et al., "Optics of Fibers and Fiber Probes," Optical–Thermal Response of Laser–Irradiated Tissue, pp. 619–666, (Pleum Press, New York, NY), 1995.

Saleh, Bahaa et al., "Fundamentals of Photonics", p. 180, (John Wiley & Sons, Hoboken, NJ), 2007.

Edmund Optics—Standard JDS Uniphase Helium–Neon Lasers, 2 pgs., 2010.

Edmund Optics—5–Color Tunable Helium–Neon Laser, 1 pg., 2010.

Newport—Helium–Neon (HeNe) Lasers—Infrared, 2 pgs., 2010.

G. Keiser, Optical Fiber Communications, McGraw–Hill, 2d. ed. 1983.

Costello, Laser Ablation of the Prostate in Patients with Benign Prostatic Hypertrophy, 1992.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-20 and 25-34 is confirmed.

Claims 21-23 are determined to be patentable as amended.

Claim 24, dependent on an amended claim, is determined to be patentable.

New claims 35-50 are added and determined to be patentable.

21. The apparatus of claim 7, wherein the tip of the waveguide comprises a fiber optic segment, the fiber optic segment including a [fiber] core [having], *wherein the core has* an outside radius R1, a bevelled end surface, and an index of refraction N1, and a core cladding having an outside radius R2, an index of refraction N2 and a cylindrical outside surface, wherein the reflecting surface comprises an interface between an external medium and the bevelled end surface on the [fiber] core at a distal end of the tip and the transmitting surface comprises a portion of the cylindrical outside surface of the core cladding, the external medium[,] having index of refraction NA, and wherein R2/R1 is greater than or equal to about N2/NA.

22. The apparatus of claim 7, wherein at least the tip of the waveguide comprises an optical fiber having a [fiber] core with a radius R1, and *a* transmissive core cladding on the [fiber] core with an outside surface defining a critical angle between the core cladding and an outside medium and a radius R2, and wherein the radius R2 is equal to or greater than about R1 divided by *a* sine of the critical angle between the core cladding and the outside medium.

23. The apparatus of claim 7, wherein the tip of the waveguide comprises a fiber optic segment, the fiber optic segment including a [fiber] core [having], *wherein the core has* an outside radius R1 and a core cladding having an outside radius R2 and a cylindrical outside surface, wherein R2 is equal to greater than about 1.4×R1; and wherein the reflecting surface comprises a bevelled surface on the [fiber] core at a distal end of the tip and the transmitting surface comprises a portion of the cylindrical outside surface of the core cladding.

*35. The apparatus of claim 1, wherein the tip comprises:*
*a transparent cap secured to the waveguide to form a sealed cavity adjacent the reflecting surface, wherein the cavity retains a selected medium adjacent to the reflecting surface.*

*36. The apparatus of claim 35, wherein the transparent cap and the waveguide are secured with one another in a region corresponding to the particular area.*

*37. The apparatus of claim 36, wherein the transparent cap and the waveguide are secured with one another in said region in a manner that reduces reflections in said region.*

*38. The apparatus of claim 36, wherein the transparent cap and the waveguide are secured with one another in said region in a manner that prevents the selected medium from entering said region.*

*39. The apparatus of claim 5, further comprising:*
*a transparent cap forming a sealed cavity adjacent the bevelled tip, wherein the cavity retains a selected medium adjacent to the bevelled tip.*

*40. The apparatus of claim 39, wherein the transparent cap is disposed in the region through which electromagnetic radiation propagating in the lateral direction from the beveled tip is transmitted.*

*41. The apparatus of claim 40, wherein the waveguide core and the transparent cap are secured with one another in a manner that reduces reflections in said region.*

*42. The apparatus of claim 40, wherein the transparent cap and the waveguide core are secured with one another in said region in a manner that prevents the selected medium from entering said region.*

*43. The apparatus of claim 7, wherein the tip comprises:*
*a transparent cap secured to the waveguide to form a sealed cavity adjacent the reflecting surface, wherein the cavity retains a selected medium adjacent to the reflecting surface.*

*44. The apparatus of claim 43, wherein the transparent cap and the waveguide are secured with one another along a region of the transmitting surface corresponding to the particular area.*

*45. The apparatus of claim 44, wherein the transparent cap and the waveguide are secured with one another in said region in a manner that reduces reflections in said region.*

*46. The apparatus of claim 44, wherein the transparent cap and the waveguide are secured with one another in said region in a manner that prevents the selected medium from entering said region.*

*47. The apparatus of claim 25, wherein the tip comprises:*
*a transparent cap secured to the waveguide to form a sealed cavity adjacent the reflecting surface, wherein the cavity maintains a selected medium adjacent to the reflecting surface.*

*48. The apparatus of claim 47, wherein the transparent cap and the waveguide are secured with one another in a region of the transmitting surface at which electromagnetic radiation reflected by the reflecting surface propagates in the second direction.*

*49. The apparatus of claim 48, wherein the transparent cap and the waveguide are secured with one another in said region in a manner that reduces reflections in said region.*

*50. The apparatus of claim 48, wherein the transparent cap and the waveguide are secured with one another in said region in a manner that prevents the selected medium from entering said region.*

* * * * *